US012340289B2

(12) United States Patent
Neumann

(10) Patent No.: US 12,340,289 B2
(45) Date of Patent: Jun. 24, 2025

(54) METHOD FOR AND SYSTEM FOR PREDICTING ALIMENTARY ELEMENT ORDERING BASED ON BIOLOGICAL EXTRACTION

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 374 days.

(21) Appl. No.: 17/690,349

(22) Filed: Mar. 9, 2022

(65) Prior Publication Data
US 2022/0198338 A1    Jun. 23, 2022

Related U.S. Application Data

(63) Continuation-in-part of application No. 17/514,453, filed on Oct. 29, 2021, which is a continuation-in-part of application No. 17/365,706, filed on Jul. 1, 2021, now Pat. No. 11,694,121, which is a continuation of
(Continued)

(51) Int. Cl.
*G06N 20/00* (2019.01)
*G06F 16/2457* (2019.01)
*G06F 18/2113* (2023.01)
*G06F 18/214* (2023.01)
(Continued)

(52) U.S. Cl.
CPC ....... *G06N 20/00* (2019.01); *G06F 16/24578* (2019.01); *G06F 18/2113* (2023.01); *G06F 18/214* (2023.01); *G06F 18/22* (2023.01); *G06F 18/2414* (2023.01)

(58) Field of Classification Search
CPC .......... G06N 20/00; G06N 7/01; G06N 20/10; G06N 5/01; G06F 16/24578; G06F 18/2113; G06F 18/214; G06F 18/22; G06F 18/24; G06F 18/2414; G06F 18/40; G06K 9/6215; G06K 9/623; G06K 9/6256; G06K 9/6273; G06Q 30/0641; G06Q 30/0201; G06Q 30/0631; G06Q 50/12; G16H 20/60; G16H 50/20
See application file for complete search history.

(56) References Cited

U.S. PATENT DOCUMENTS 9,898,788 B1    3/2018  Calargun et al.
2018/0240542 A1*    8/2018  Grimmer ............... A61P 25/00

* cited by examiner

*Primary Examiner* — Ruiping Li
(74) *Attorney, Agent, or Firm* — Caldwell Intellectual Property Law

(57) ABSTRACT

A system for predicting alimentary element ordering based on biological extraction includes a computing device configured to identify an alimentary profile, wherein identifying further comprises obtaining a biological extraction of a user, determining an alimentary element order chronicle of a user, and identifying the alimentary profile as a function of the biological extraction and the alimentary element order chronicle, determine an edible of interest, wherein determining the edible further comprises receiving a datum as a function of an edible database, and determining the edible of interest as a function of the alimentary profile and the datum, obtain a nourishment information associated to the edible of interest, and generate a nourishment score as a function of the edible of interest and the nourishment information.

20 Claims, 11 Drawing Sheets

Related U.S. Application Data application No. 17/087,745, filed on Nov. 3, 2020, now Pat. No. 11,100,430.

(51) Int. Cl.
*G06F 18/22* (2023.01)
*G06F 18/2413* (2023.01)

METHOD FOR AND SYSTEM FOR PREDICTING ALIMENTARY ELEMENT ORDERING BASED ON BIOLOGICAL EXTRACTION

CROSS-REFERENCE TO RELATED APPLICATIONS

This application is a continuation-in-part of Non-provisional application Ser. No. 17/514,453 filed, on Oct. 29, 2021 and entitled "METHOD FOR AND SYSTEM FOR ARRANGING CONSUMABLE ELEMENTS WITHIN A DISPLAY INTERFACE" this application is a continuation-in-part of Non-provisional application Ser. No. 17/365,706 filed on Jul. 1, 2021 and entitled "METHOD FOR AND SYSTEM FOR PREDICTING ALIMENTARY ELEMENT ORDERING BASED ON BIOLOGICAL EXTRACTION," which is a continuation of Non-provisional application Ser. No. 17/087,745 filed on Nov. 3, 2020, and entitled "METHOD FOR AND SYSTEM FOR PREDICTING ALIMENTARY ELEMENT ORDERING BASED ON BIOLOGICAL EXTRACTION," each of the Non-provisional application Ser. No. 17/514,453 and Non-provisional application Ser. No. 17/365,706 and Non-provisional application Ser. No. 17/087,745 is hereby incorporated by reference herein in its entirety.

FIELD OF THE INVENTION

The present invention generally relates to the field of machine-learning. In particular, the present invention is directed to systems and methods for predicting alimentary element ordering based on biological extraction.

BACKGROUND

Alimentary element originators often provide alimentary elements for dine-in, take-out, and delivery. Individuals may interact with an alimentary maker via a device such as a computer or smartphone to place an order. One caveat with customer ordering with alimentary element take-out and delivery services is time lag involved in the process. Individuals may place orders when a need for the order arises, but alimentary elements may not arrive until long after. Furthermore, individuals may wade through a variety of options that are not beneficial to the user and locating suitable alimentary elements and alimentary element originators may be difficult.

SUMMARY OF THE DISCLOSURE

In an aspect, an apparatus for predicting alimentary element ordering based on biological extraction includes at least a processor and a memory communicatively connected to the at least a processor, the memory containing instructions configuring the at least a processor to identify a plurality of edibles, wherein identifying the plurality of edibles further comprises, obtaining an alimentary element chronical of a user, generating an alimentary profile, as a function of the biological extraction, and identifying the plurality of alimentary elements as a function of the alimentary profile, generate, for the plurality of edibles, a plurality of nourishment scores, wherein generating the plurality of nourishment scores includes generating, for each edible of the plurality of edibles, a nourishment score as a function of the edible and the alimentary profile, ordering the plurality of edibles according to the plurality of nourishment scores, and displaying the ordered plurality of edibles.

In another aspect, a method of predicting alimentary element ordering based on biological extraction includes identifying, by a computing device, a plurality of edibles, wherein identifying the plurality of edibles further includes obtaining an alimentary element chronical of a user, generating an alimentary profile, as a function of the biological extraction, and identifying the plurality of alimentary elements as a function of the alimentary profile, generating, by the computing device and for the plurality of edibles, a plurality of nourishment scores, wherein generating the plurality of nourishment scores includes generating, for each edible of the plurality of edibles, a nourishment score as a function of the edible and the alimentary profile, ordering, by the computing device, the plurality of edibles according to the plurality of nourishment scores, and displaying, by the computing device the ordered plurality of edibles.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for predicting alimentary element ordering based on biological extraction. Embodiments may perform alimentary element predictions based on a user's biological extraction and alimentary element order chronicle and suggest predicted alimentary elements based on predictions. In an embodiment, computing device may locate alternative alimentary elements based on classifying alimentary element metrics in the predicted alimentary elements, wherein the alternative alimentary element is more beneficial to a user's biological extraction parameters.

Figure 1:
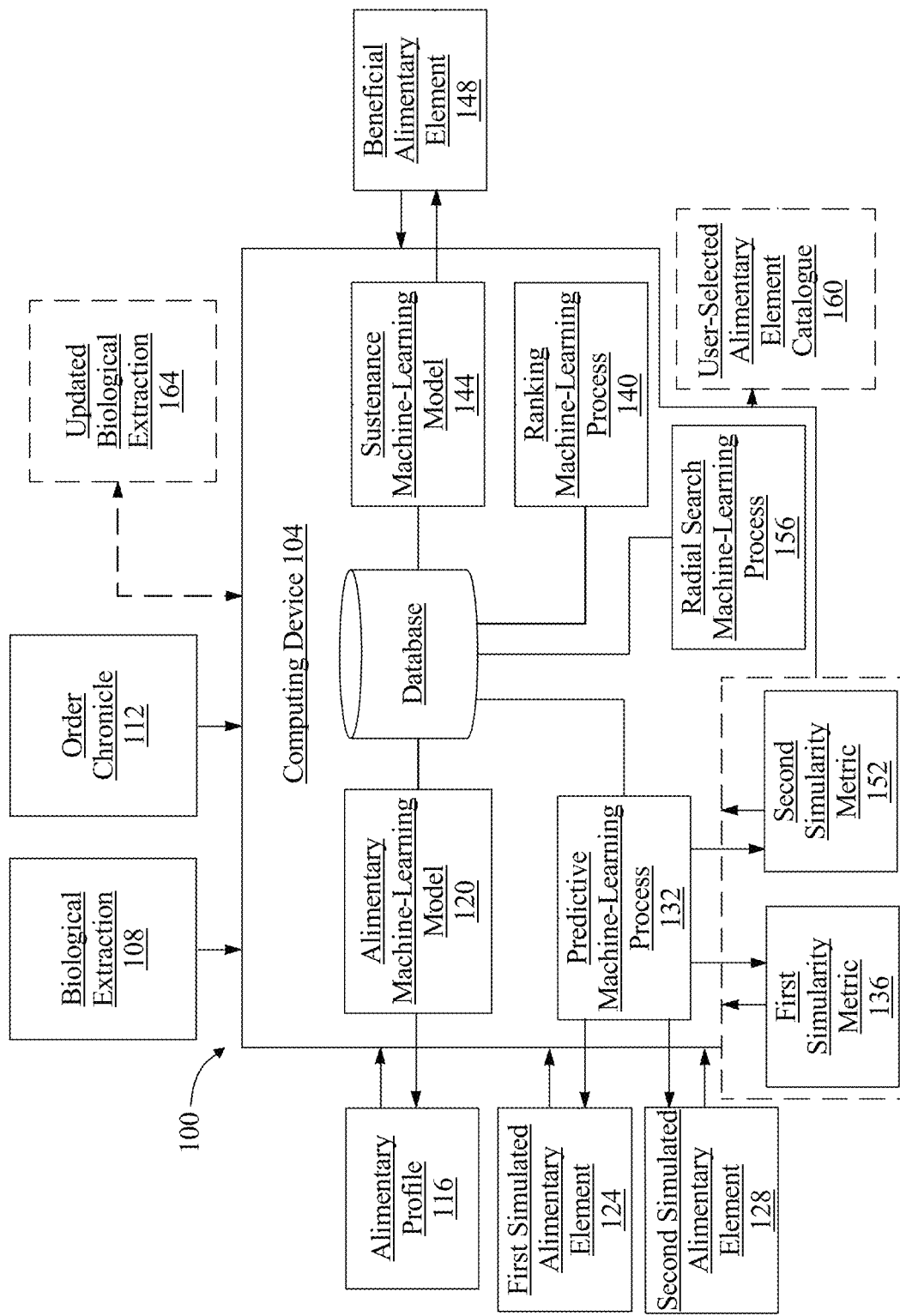
FIG. 1 is a block diagram illustrating an exemplary embodiment of a system for predicting alimentary element ordering based on biological extraction.

Referring now to FIG. 1, an exemplary embodiment of a system 100 predicting alimentary element ordering based on biological extraction is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing in reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is configured to receive a biological extraction of a user. A "biological extraction," as used in this disclosure, is any biological, chemical, physiological, etc. data that is associated with the user. Biological extraction 108 data may include medical histories, diseases, surgeries, injuries, symptoms, exercise frequency, sleep patterns, lifestyle habits, and the like, that may be used to inform a user's diet. Biological extraction 108 data may include diet information such as nutrition deficiencies, food intolerances, allergies, and the like. Biological extraction 108 data may alternatively or additionally include a plurality of dimensions of biological extraction 108 data any data used as a biological extraction as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, computing device 104 is configured to receive an alimentary element order chronicle. An "order chronicle," as used in this disclosure is a chronological history of transactions associated with a user involving alimentary elements. An "alimentary element," as used in this disclosure, is a meal, grocery item, food element, nutrition supplement, edible arrangement, or the like, that may be generated by an alimentary element originator. An "alimentary element originator," as used in this disclosure, is a restaurant, cafeteria, fast food chain, grocery store, food truck, farmer's market, proprietor, convenience store, deli, or any place that may provide an alimentary item. An alimentary element originator, as used in this disclosure, may be simply referred to as 'originator'. An order chronicle 112 may include all alimentary elements a user may have ordered via a mobile app, web-browser, in-person, via phone, or any other method, for take-out, dine-in, and/or delivery. An order chronicle 112 may include all alimentary elements a user may have obtained at a grocery store. An order chronicle 112 may include a chronological history wherein the dates and times of alimentary elements a user has ordered and/or otherwise obtained is included in the order chronicle.

Continuing in reference to FIG. 1, receiving the alimentary element order chronicle 112 may include generating training data using the alimentary element order chronicle 112 to train the alimentary element machine-learning model to identify user alimentary element patterns. Order chronicle 112, as used herein for system 100, may include data regarding user alimentary element patterns. As used in this disclosure, "user alimentary element patterns," may include patterns, heuristics, behaviors, or any other relationships, that computing device 104 may make concerning the data in the order chronical of a user. An alimentary element patterns may include data that indicates a user preferably orders a particular type of alimentary element or from a particular originator, for instance a fast-food originator, only during particular times, such as during evenings, on weekends, etc. An alimentary element patterns may include a pattern that a user avoids alimentary elements containing a particular ingredient, such as tree nuts, lactose, etc. As used in this disclosure, an alimentary element pattern may be simply referred to as an "order behavior" and/or "order pattern."

Continuing in reference to FIG. 1, computing device 104 is configured to retrieve an alimentary profile. Computing device 104 may retrieve an alimentary profile via a database, such as a NoSQL database and/or any relationship database, online research repository, or the like. Computing device 104 may retrieve an alimentary profile using a machine-learning process, as described herein, wherein the machine-learning process may know to retrieve an alimentary profile, data relating to an alimentary profile and/or a plurality of alimentary profile to perform a function, as described herein. Retrieval of an alimentary profile may include using a machine-learning process, such as a predictive machine-learning process, to retrieve the alimentary profile, as described in further detail below.

Continuing in reference to FIG. 1, computing device 104 is configured to determine an alimentary profile, wherein determining the alimentary profile includes generating an alimentary element model. An "alimentary profile," as used in this disclosure, is a collection of data that described a user's ordering behaviors as it relates to relationships between the content of a user's ordering history and the user's biological extraction data. For instance, an alimentary profile 116 may be a profile that indicates a user has a plurality of allergies and/or intolerances present from data in a biological extraction, and that the user has acknowledged an allergy by avoiding certain alimentary elements. Additionally, an alimentary profile 116 may include relationships that indicate a user exhibits ordering behavior, alimentary element patterns, and the like, according to their order chronicle 112, that they prefer alimentary elements that do not benefit their health, according to biological extraction 108 data.

Continuing in reference to FIG. 1, determining the alimentary profile using an alimentary machine-learning model includes training the alimentary machine-learning model with training data that includes a plurality of entries wherein each entry relates user biological extraction 108 to alimentary element order chronicle 112. Training data may originate from the data present in a user's biological extraction and a user's order chronicle, as described above. An alimentary machine-learning model may be generated by a computing device 104 performing a machine-learning algorithm and/or process by using a machine-learning module, as described in further detail below. Training alimentary machine-learning model 120 with training data may result in a model that contains a variety of qualitative and/or quantitative patterns, heuristics, or the like, that describe relationships between biological extraction 108 and alimentary element order chronicle 112. In non-limiting illustrative examples, alimentary machine-learning model 120 may contain a plurality of individual functions, vectors, matrices, and the like, which describe individual user ordering behaviors as it relates to biological extraction data. In further non-limiting illustrative examples, alimentary machine-learning model 120 may be used by computing device 104 to determine an alimentary profile 116 using the plurality of individual functions, vectors, matrices, and the like, wherein the computing device 104 may include all the patterns, correlations, and/or heuristics into a single profile. Alimentary profile 116 may be used as a reference profile which computing device 104 may use as a rubric for determining alimentary elements which correspond to alimentary elements a user would preferentially order and/or alimentary elements that may benefit a user's health.

Continuing in reference to FIG. 1, computing device 104 may generating the alimentary profile as a function of the alimentary machine-learning model. Model may include at least a mathematical relationship between user alimentary element patterns and user biological extraction 108 data, wherein the mathematical relationship describes how user alimentary element patterns affect user biological extraction 108 parameters. For instance and without limitation, an alimentary profile 116 may include data that demonstrates that a user's biological extraction 108 data such as a history of high blood pressure and elevated resting heart rate may be correlated to an order chronicle of alimentary elements that are high sodium, such as smoked, cured, salted, and/or canned meat, poultry, fish, bacon, cold cuts, frozen dinners, canned entrees, and the like. In such an example, the order chronicle 112 may include the cause of the user's biological extraction 108 data, wherein if the order chronicle 112 could be changed over time to eliminate the offending alimentary elements, and results in the biological extraction 108 data indicated improved health. An alimentary profile 116 may be used to indicate which alimentary elements of a user's order chronicle 112 are beneficial to their overall health, and which are harmful to the user's overall health. An alimentary profile 116 may indicate instances wherein ordering history is dictated by biological extraction data and instances where ordering history effects, contributes to, or potentially explains elements of data in a biological extraction. Alimentary profile 116 may include mathematical relationships derived from an alimentary machine-learning model illustrating such data, as described in further detail below.

Continuing in reference to FIG. 1, computing device 104 is configured to identify, using the alimentary profile 116 and a predictive machine-learning process, a predicted alimentary element and an alternative alimentary element. A "predicted alimentary element," as used in this disclosure, is an alimentary element that a user is predicted to order according to the data contained in the user's alimentary profile 116, biological extraction 108, and order chronicle 112. A predicted alimentary element 124 may be the same item that a user has previously ordered. A predicted alimentary element 124 may be a predicted alimentary element that a user has not before ordered according to a user's order chronicle 112. For instance, a user may be in a new region, with originators that are foreign to the user, and system 100 may generate a predicted alimentary element 124 for a user, despite the user not being aware of the alimentary elements available to them. A "alternative alimentary element," as used in this disclosure is an alternative alimentary element that is an alimentary element predicted generated by a computing device 104 as an alternatively to a predicted alimentary element, wherein the alternative alimentary element is more beneficial to a user's biological extraction 108 data. For instance and without limitation, a predicted alimentary element 124 may be a buffalo chicken sandwich, wherein the chicken is breaded and the buffalo sauce contains lactose, and an alternative alimentary element 128 is a buffalo chicken sandwich with grilled chicken and buffalo sauce without lactose. In such an example, the alternative alimentary element 128 may be from the same originator as a predicted alimentary element 124, but with modifications. Alternatively or additionally, the alternative alimentary element 128 may be from a different originator as a predicted alimentary element 124.

Continuing in reference to FIG. 1, computing device 104 is configured for determining, using the predictive machine-learning process and the alimentary profile 116, the predicted alimentary element 124, wherein the predicted alimentary element 124 is a predictive alimentary element a user is expected to order. A predictive machine-learning process 132 may be generated by a computing device 104 performing a machine-learning algorithm and/or process by using a machine-learning module, as described in further detail below.

Continuing in reference to FIG. 1, generating the predicted alimentary element 124 may include identifying a temporally anterior alimentary element present in the user alimentary element order chronicle 112. Identifying a temporally anterior alimentary element may include searching, by computing device 104, a user's order chronicle 112 for discrete alimentary elements, such as individual alimentary elements that may be obtained from an originator. As used in this disclosure, an "temporally anterior alimentary element," is an alimentary element that has been consumed by user temporally anterior, or any point in time prior to initiating system 100, which may include an alimentary element as part of order chronicle 112, an alimentary element indicated by user input via graphical user interface, an alimentary element input via a second application for tracking alimentary elements, or the like. Computing device 104 may identify using individual alimentary elements indicated by a user as inputs via a graphical user interface, as described in further detail below. Identifying alimentary elements may include identifying a list of ingredients, prices, and nutrition facts of an alimentary element. For instance, if an order chronicle 112 indicates a Cobb salad from originator X, wherein the computing device may identify that a Cobb salad from originator X corresponds to an alimentary element that was $12.99, including chopped greens, tomato, bacon crisps, roasted chicken breast, hard-boiled eggs, avocado, chives, Roquefort cheese, and red-wine vinaigrette, with 730 calories, 30 grams protein, 53 grams fat, and 35 grams carbs.

Continuing in reference to FIG. 1, generating the predicted alimentary element 124 may include searching, using the alimentary profile 116 and the predictive machine-learning process 132, for a plurality of alimentary elements, wherein searching includes identifying alimentary element metrics present in the temporally anterior alimentary element, and locating the plurality of alimentary elements containing similar alimentary element metrics. As used in this disclosure, an "alimentary element metric" is an element of data that can be used to discriminate between alimentary elements, including price, ingredients, name, originator, nutrition facts, and the like. As used in this disclosure, "an alimentary element metric" may simply be referred to as "a metric." Computing device 104 may identify an alimentary element, including all alimentary element metrics, and search for a plurality of alimentary elements. Searching for a plurality of alimentary element may include locating alimentary elements with identical ingredients. Searching for a plurality of alimentary elements may include locating alimentary elements with similar ingredients. Searching for a plurality of alimentary elements may include locating alimentary elements from the same originator, or a different originator. Searching may be performed by computing device 104 using a web-browser, mobile application, restaurant menu, grocery store inventory, database, research repository, or any other suitable source of alimentary element information. In non-limiting illustrative examples, a search based on ingredients from a Cobb salad may return other salad types such as a grilled chicken salad, Caesar salad, and the like. In further non-limiting illustrative examples, a search may return alimentary elements that are not salads but share the ingredients, such as a bacon, chicken, avocado wrap with tomato, chopped greens, a dressing, and a cheese.

Continuing in reference to FIG. 1, generating the predicted alimentary element 124 may include generating at least an alimentary element metrics for each of the plurality of alimentary elements. Each identified alimentary element from the search according to alimentary element metrics, as described above, may have its alimentary element metrics retrieved. Computing device 104 may generate a file wherein each element of the file is a queried alimentary element associated with a list of alimentary element metrics. For instance, each queried alimentary element may have associated with it an originator location from where the alimentary element was identified, ingredients, price, alimentary element name, and nutrition facts. For instance, in non-limiting illustrative examples, a queried alimentary element may be a bacon-chicken-avocado wrap from originator Y, with a price of $12.00 and ingredient list of chicken, bacon, avocado, whole wheat tortilla wrap, tomato, chopped greens, a cheese, and a dressing, and nutrition facts of 820 calories, 49 grams fat, 57 gram carbohydrates, and 41 grams protein. All alimentary elements of the plurality of alimentary elements identified by the search performed by computing device 104 may contain this data in the file.

Continuing in reference to FIG. 1, generating the predicted alimentary element 124 may include calculating, using the alimentary element metrics, a first similarity metric between the temporally anterior alimentary element and each of the plurality of alimentary elements. A "first similarity metric," is a numerical value that measures a relationship between alimentary element metrics of a predicted alimentary element and any temporally anterior alimentary element that may have been identified from a user's order chronicle. A first similarity metric 136 may be calculated as a function of similarity to a predicted alimentary element 124. For instance and without limitation, first similarity metric 136 may be a numerical value that is a percent similarity between two ingredient sets, wherein out of 10 ingredients, an alimentary element contains 8 ingredients, it would have 80% similarity. In non-limiting illustrative examples, a first similarity metric 136 may be calculated from a comparison of price between a predicted alimentary element and an alimentary element in an order chronicle, wherein the metric is scaled on a factor of 1.0 where 1.0 equals an exact price match. In further examples, a metric of 1.2 would be a 20 percent increase in price, wherein a score of 0.5 would be half the price, with smaller metrics representing less costly alimentary elements, and the price would be bound at 0.0 for "free", such as an alimentary element from a party, event, or the like. Persons skilled in the art, upon review of this disclosure in its entirety, will be aware the various ways in which a first similarity metric 136 could be generated to compare alimentary metrics between any two pairing of alimentary elements, wherein one of the alimentary elements is the predicted alimentary element 124.

Continuing in reference to FIG. 1, generating the predicted alimentary element 124 may include ranking, using a ranking machine-learning process, the plurality of alimentary elements based on the first similarity metrics 136. Ranking machine-learning process may include any machine-learning algorithm and/or process performed by using a machine-learning module, as described in further detail below. Ranking machine-learning process 140 may accept an input that is a plurality of similarity metrics, including an associated plurality of alimentary elements, and generate an output that is a ranked list of the plurality of alimentary elements based on the similarity metrics. For instance and without limitation, ranking machine-learning process 140 may rank the similarity metrics in such a way that the highest ranking corresponds to alimentary elements that represent matches to outputs of a predicted alimentary element 124. A ranking machine-learning process 140 may rank using a formula, equation, function, or the like, that takes into account similarity metrics from comparing prices, ingredient lists, originator location, among other alimentary element metric categories.

Continuing in reference to FIG. 1, generating the predicted alimentary element 124 may include selecting the predicted alimentary element 124 based on the ranking of the plurality of alimentary elements. Ranking machine-learning process 140 may generate an output of ranked alimentary elements, wherein computing device 104 may select an alimentary element to be the predicted alimentary element 124 based on the ranking.

Continuing in reference to FIG. 1, computing device 104 is configured for generating, using the predicted alimentary element 124, the alternative alimentary element 128, wherein generating includes creating a classifier, using a classification machine-learning process, wherein the classifier contains alimentary element metrics of the predicted alimentary element. A "classifier" may be configured to output at least a datum that labels or otherwise identifies a set of data that are clustered together, as described in further detail below. A classifier may represent a body of data that is a series of alimentary element metrics describing a predicted alimentary element. In non-limiting illustrative examples, a classifier may relate to the price, ingredients, nutrition facts, and originator of a predicted alimentary element that may be a packet of data used to search or otherwise identify an alternative alimentary element.

Continuing in reference to FIG. 1, generating the alternative alimentary element may include generating a sustenance machine-learning model, wherein the sustenance machine-learning model is trained with training data that includes a plurality of entries wherein each entry relates user biological extraction to alimentary elements that have beneficial effects on user biological extraction parameters. Sustenance machine-learning model may be generated by a computing device 104 performing a machine-learning algorithm and/or process by using a machine-learning module, as described in further detail below. Training data for sustenance machine-learning model 144 may include data that is categorized using a classifier, as described above. Classifier may describe alimentary elements for a subset of users with alike biological extraction 108, order chronicle 112, and/or other data, metrics, and the like. Alternatively or additionally, sustenance machine-learning model 144 may be trained with training data that contains a single user's biological extraction 108 data and determines which alimentary elements may be beneficial to that user.

Continuing in reference to FIG. 1, as used in this disclosure, a "beneficial alimentary element," is any alimentary element that improves a user's biological extraction 108 parameters. Improvement of biological extraction 108 parameters may refer to driving a user's biological extraction parameters into a normal, or otherwise healthy range, for their age, sex, height, etc. For instance and without limitation, a user's consumption patterns may be carbohydrate heavy, leading to a state of prolonged increased blood sugar, wherein blood sugar levels have established thresholds for 'normal' and/or 'healthy' among individuals. In such an example, a beneficial alimentary element 148 may be an alimentary element that provides satiety similar to a first alimentary element that user would choose but has a reduced glycemic index. A beneficial alimentary element 148 may be any alimentary element that avoids a user's allergies, food intolerances, and/or any negative or unintended effect on a user's biological extraction, including effects a user was not initial aware. In non-limiting illustrative examples, sustenance machine-learning model 144 may be a model trained to output alimentary elements that may improve a user's biological extraction by training with data that reveals patterns, heuristics, or any other qualitative and/or quantitative relationships between the effect alimentary elements may have on biological extraction 108, and how this may effect a user's current biological extraction 108 or ordering behaviors. In some cases, an alimentary element that may be beneficial among users will be the same, or similar; however, an alternative alimentary element 128 based on a predicted alimentary element 124 using the relationships in the sustenance machine-learning model 144 may result in different results among users due to taking into account food preferences and individual differences in biological extraction 108.

Continuing in reference to FIG. 1, computing device 104 generating the alternative alimentary element may include searching, using the sustenance machine-learning model 144, for a plurality of beneficial alimentary elements 148. Computing device 104 may use the relationships captured in the sustenance machine-learning model 144 and the generated outputs of at least a beneficial alimentary element 148 to search for a plurality of beneficial alimentary elements 148. Computing device 104 may search any source, as described above. In non-limiting illustrative examples, computing device 104 may search using the predicted alimentary element 124 and/or any alimentary element metric of a predicted alimentary element 124. For instance and without limitation, a computing device 104 may search for beneficial alimentary elements 148 that are similar to a first beneficial alimentary element 148 output by the model with a criterion of having at least one ingredient in common with a predicted alimentary element 124. In further non-limiting illustrative examples, computing device 104 may search for a plurality of beneficial alimentary elements 148 using alimentary element metrics of a first beneficial alimentary element 148 output by a sustenance machine-learning model 144. Sustenance machine-learning model 144 may generate the plurality of beneficial alimentary elements 148 as an output from the training data used to train the model.

Continuing in reference to FIG. 1, computing device 104 generating the alternative alimentary element 128 may include may retrieving alimentary element metrics of the plurality of beneficial alimentary elements 148. Each identified beneficial alimentary element 148 from a search, as described above, may have its alimentary element metrics retrieved, as described above. Computing device 104 may generate a file wherein each element of the file is a queried beneficial alimentary element 148 associated with a list of alimentary element metrics. For instance, each queried alimentary element may have associated with it an originator location from where the alimentary element was identified, ingredients, price, alimentary element name, and nutrition facts, as described above.

Continuing in reference to FIG. 1, computing device 104 generating the alternative alimentary element 128 may include calculating a second similarity metric based on similarity of the alimentary element metrics of the plurality of beneficial alimentary elements and the predicted alimentary element. As used in this disclosure, "second similarity metric" is a numerical value that measures a relationship between alimentary element metrics of a predicted alimentary element 124 and any beneficial alimentary element 148. For instance and without limitation, second similarity metric 152 may be a numerical value that is a percent similarity between two ingredient sets, wherein out of 10 ingredients, a beneficial alimentary element 148 shares 4 ingredients with a predicted alimentary element 124, it would have 40% similarity. In non-limiting illustrative examples, a distinction between a first similarity metric 124 and a second similarity metric 152 may be that a first similarity metric 124 relates to similarity between alimentary elements identified in a user's order chronicle and the predicted alimentary element 124 output from system 100; a second similarity metric 152 relates to similarity between a predicted alimentary element 124 and a beneficial alimentary element 148 that may represent a candidate to replace it. Persons skilled in the art, upon review of this disclosure in its entirety, will be aware the various ways in which a second similarity metric 152 could be generated to compare alimentary metrics between any two pairing of alimentary elements, wherein one of the alimentary elements is a beneficial alimentary element 148.

Continuing in reference to FIG. 1, computing device 104 generating the alternative alimentary element 128 may include ranking, using the ranking machine-learning process 140, the plurality of beneficial alimentary elements 148 based on the second similarity metric 152. Ranking machine-learning process 140 may rank beneficial alimentary elements using the second similarity metrics 152 as was done with ranking the predicted alimentary elements using the first similarity metrics 136, as described above.

Continuing in reference to FIG. 1, computing device 104 generating the alternative alimentary element 128 may include selecting the alternative alimentary element 128 based on the ranking, wherein the alternative alimentary element 128 is selected from the plurality of beneficial alimentary elements 148. Computing device 104 may select the alternative alimentary element 128 as a function of the ranking as was done for selecting a predicted alimentary element 124 as a function of its ranking. In non-limiting illustrative examples, ranking machine-learning process 140 may generate an output that is a ranked list of beneficial alimentary elements 148, wherein a top-ranked output in the list is a beneficial alimentary element 148 that most benefits a user's biological extraction and/or is most similar to a predicted alimentary element 124 based on the plurality of factors in the alimentary metrics of each alimentary element. Computing device 104 may select a beneficial alimentary element 148 as a function of the ranking to represent an output that is the alternative alimentary element 128.

Continuing in reference to FIG. 1, computing device 104 generating the alternative alimentary element 128 is configured for ranking alimentary elements as a function of effect to a user's biological extraction if substituted for the predicted alimentary element 124. Ranking machine-learning process 140 may be used to rank beneficial alimentary elements 148 as a function of effect on a user's biological extraction 108. For instance and without limitation, ranking machine-learning process 140 may rank outputs of system 100, including predicted alimentary element 124, order chronicle 112 alimentary elements, beneficial alimentary elements 148, and alternative alimentary element 128, to provide user comprehensive effect on biological extraction 108 as a function of order behaviors. Ranking machine learning-process may rank alimentary elements based on effect on biological extraction using the relationships described in the sustenance machine-learning model 144 which is trained on how alimentary elements may affect biological extraction 108. In non-limiting illustrative examples, such a sustenance machine-learning model 144 may be trained with a classifier relating to types of alimentary elements, types of users, elements of biological extraction data 108 to locate and refine relationships, patterns, functions, models, and the like. Computing device 104 may select an alimentary element to be an alternative alimentary element 128 as a function of effect on a user's biological extraction 108.

Continuing in reference to FIG. 1, computing device 104 is configured to generate a representation via a graphical user interface of the predicted alimentary element 124 and the alternative alimentary element 128 to a user. A "graphical user interface," as used in this disclosure, is any form of a user interface that allows a user to interface with an electronic device through graphical icons, audio indicators, text-based interface, typed command labels, text navigation, hyperlinked elements, and the like, wherein the interface is configured to provide information to the user and accept input from the user. Computing device 104 may generate a representation of the predicted alimentary element 124 via a graphical user interface using any mapping application or algorithm, for instance and without limitation, a web-based navigation application such, a mobile navigation application, or the like. Computing device 104 may use any mapping application in combination with a user's geophysical location to determine nearby originators which may provide a predicted alimentary element 124. A "geophysical location," as used in this disclosure, is an address, longitude and/or latitude position, global position system (GPS) coordinates, or the like, that system 100 may use to identify originators nearby a user and retrieve alimentary element data. As used herein, geophysical location may be simply referred to as "geophysical data," which means geophysical data concerning at least a location. Computing device 104 may similarly generate a representation of the predicted alimentary element 124 via a graphical user interface using any mapping application or algorithm, for instance and without limitation, a web-based navigation application such, a mobile navigation application, or the like. Persons skilled in the art, upon review of this disclosure in its entirety, will be aware of the various ways in which a computing device 104 may display to a user a physical transfer path via a graphical user interface, and be aware the various navigation applications that may be used to communicate a physical transfer path.

Continuing in reference to FIG. 1, providing the representation of the predicted alimentary element 124 and the alternative alimentary element 128 may include queuing the predicted alimentary element 124 and the alternative alimentary element 128 with an alimentary element originator, wherein queuing includes locating a first alimentary element originator with at least a metric that matches the predicted alimentary element 124 or the alternative alimentary element 128 within a first distance of a user. Computing device 104 may search within a first radius of a user for alimentary element originators including associated data, for instance and without limitation hours of operation, geophysical location, etc. Computing device 104 may locate an alimentary element originator and retrieve an alimentary element repository, such as a menu, item list, etc. In non-limiting illustrative examples, computing device 104 may restrict search locally, for instance if a user is in a grocery store, computing device 104 may search the grocery store for alimentary elements that are a predicted alimentary element 124 and/or an alternative alimentary element 128. In such an example, a user may indicate via the graphical user interface to computing device 104 to locate the ingredients for predicted alimentary element 124 that may include obtaining and purchasing a plurality of ingredients to prepare predicted alimentary element 124. In this case, computing device 104 may function as a shopping list for replicating the predicted alimentary element 124 and/or an alternative alimentary element 128. In further non-limiting illustrative examples, user may be prompted to select, or otherwise indicate, a particular predicted and/or alternative alimentary element and computing device 104 may determine if the ingredients are present at the current grocery store, cycling through options until one is identified. In such an example, computing device may present the ingredient list to the user for shopping purposes, adding to the order chronicle 112.

Continuing in reference to FIG. 1, computing device 104 may queue a predicted alimentary element 124 or an alternative alimentary element 128. A "queue," as used in this disclosure, is a collection of alimentary elements that are maintained in a sequence and can be modified by the addition of entities and removal of entities from the sequence via an interactive interface with a user. In non-limiting illustrative examples, the queue may have an "active end" and a "reserve end," wherein the active end is the predicted alimentary element 124 and/or alternative alimentary element 128 that has been located by the computing device 104 in a nearby alimentary element originator; additionally, there may be related alimentary elements that are in the queue "behind" the predicted alimentary element 124 and alternative alimentary element 128 nearer the reserve end. In further non-limiting illustrative examples, a user may indicate via the graphical user interface that they do not want a predicted alimentary element 124, whereby computing device 104 may remove it from the active end and push up by one place the other alimentary elements in the queue. In such an example, computing device 104 may add a newly generated alimentary element to the reserve end to maintain a list that a user may view, scroll through, or the like. Computing device 104 may locate an alimentary element originator for each alimentary element in the queue; alternatively or additionally, computing device 104 may restrict searches to the most 'active end' entity in the queue or to an alimentary element that a user as selected.

Continuing in reference to FIG. 1, providing the representation of the predicted alimentary element and the alternative alimentary element may include addressing a user to order an alimentary element of the predicted alimentary element 124 and the alternative alimentary element 128. Computing device 104 may prompt a user, via the graphical user interface, to order the predicted alimentary element 124 or the alternative alimentary element 128. Computing device 104 may queue alimentary elements, as described above, and user may have the option to indicate a selection of an alimentary element. In non-limiting illustrative examples, user may be prompted to indicate selection of the predicted alimentary element 124, but rather selects that they do not want the predicted alimentary element 124 and prefers a healthier option, wherein the queue moves up the second option, providing an alternative alimentary element 128, again prompting the user.

Continuing in reference to FIG. 1, providing the representation of the predicted alimentary element 124 and the alternative alimentary element 128 may include prompting a user to order from a plurality of substitute alimentary options. A "substitute alimentary options," as used in this disclosure, are alternative alimentary elements 128 generated by computing device 104 according to a user input. Computing device 104 may provide substitute alimentary options depending on a particular alimentary metric associated with a predicted alimentary element 124 and/or alternative alimentary element 128. For instance and without limitation, a user may want alimentary elements that are 'plant-based only' and communicate via textual-based interface for computing device 104 to generate alternative alimentary elements 128 that a user may enjoy according to order chronicle and biological extraction. In non-limiting illustrative examples, a user may indicate that they want a vegan option version of a non-vegan meal identified in their order chronicle 112; computing device 104 may provide a plurality of substitute alimentary options based on the user-indicated stipulation of vegan options.

Continuing in reference to FIG. 1, providing the representation of the predicted alimentary element 124 and the alternative alimentary element 128 may include generating an audiovisual notification for addressing a user to select from a plurality of alternative alimentary elements. An "audiovisual notification," as used in this disclosure, is a piece of information that alerts a subject to ordering an alimentary element. An audiovisual notification may be a textual alert, a graphic, a vibration alert, a sound, or any other audiovisual notification, or combination thereof, that computing device 104 may provide a user. Audiovisual notification may include addressing the user to select an alimentary element, for instance from the plurality of alternative alimentary elements 128. Persons skilled in the art, upon review of this disclosure in its entirety, will be aware of the various ways in which a system 100 may provide an audiovisual notification to a user for ordering.

Continuing in reference to FIG. 1, addressing a user to order from a plurality of alternative alimentary elements 128 may include using a radial search machine-learning process, wherein the radial search machine-learning process determines a first distance, and searches the first distance for an alternative alimentary element originator, wherein the user can order at least an alternative alimentary element 128 from the alternative alimentary element originator. Ordering from the plurality of substitute alimentary options may include using a radial search machine-learning process, wherein the radial search machine-learning process determines a first radius, and searches the first radius for an alternative alimentary element originator, wherein the user can order at least a substitute alimentary element option from the alternative alimentary element originator. A radial search machine-learning process may include machine-learning algorithms, processes, and/or model, performed by a machine-learning module, as described in further detail below. Radial search machine-learning process 156 may execute a radial search, wherein the radial search machine-learning process 156 may find approximate solutions to combinatorial problems. Combinatorial problems involve finding a grouping, ordering, clustering, or assignment of a discrete, finite set of objects that satisfies given conditions.

Continuing in reference to FIG. 1, radial search machine-learning process 156 may accept an input of a user geophysical location and an alimentary element identity and search within a first radius for an alimentary element originator, search the originator for an alimentary element that satisfies a substitute alimentary element, generating an output that describes the alimentary element, geophysical location, and originator identity. Alternatively or additionally, radial search machine-learning process may begin with a first alimentary element originator geophysical location and menu, ingredient list, etc. as a "local solution" and select the first alimentary element originator geophysical location as the center for the first radial search. Radial search machine-learning process may be used to determine an originator for any alimentary element described herein, including for instance and without limitation, a predicted alimentary element 124 and/or alternative alimentary element 128, as described above. Radial search machine-learning process 156 may place the input data on a 2-Dimensional grid, for instance and without limitation, using a mapping application or algorithm, for instance and without limitation, a web-based navigation application such, a mobile navigation application, or the like, that may relate geophysical location in a predetermined area base on a first location using a computing device 104 and/or user device. Radial search machine-learning process 156 may use such an accessible mapping tool, application, and/or algorithm for radial search.

Continuing in reference to FIG. 1, radial search machine-learning process 156 may employ a radial search approach using the concept of rings, wherein each ring is a particular distance about a location, which defines the location and size of search areas, perhaps about a current 'good' solution. For instance, a predicted alimentary element 124 and first alimentary element originator may be a current 'good' solution, but a radial search may indicate a larger ring about an originator for the predicted alimentary element 124, searching further from that location. Radial search iteratively modifies the radii of these rings, and generates new centers, to cover the search space. A concentration step corresponds to choosing a solution as the center of a new ring. An expansion step corresponds to the exploration around a given center by increasing and reducing the radius of the ring until a better solution other than the current center is found. A "better solution" may include an alimentary element originator that is nearer to a user, contains a predicted alimentary element 124, contains an alternative alimentary element 128, among other criteria. This dynamic process of centration and expansion of the search is repeated until a stopping condition is met. A stopping condition, for instance and without limitation, may be an originator that supplies an alimentary element a user has indicated is suitable, or otherwise a match to an alimentary element in the queue, and/or an alimentary element that is a minimal distance from user current geophysical location.

Continuing in reference to FIG. 1, radial search machine-learning process 156 may use any form of proximity search or any algorithm used for solving an optimization problem of locating the point (originator) in a given set that is closet to a given point (user). Radial search algorithms, methods, and computational processes that radial search machine-learning process 156 may use, as described herein, may include exact methods of proximity search including linear search and space partitioning; approximation methods such as Greedy search in proximity neighborhood graphs, locality sensing hashing, nearest neighbors search in spaces with small intrinsic dimension, projected radial search, vector approximation filing, and compression/clustering based search. Alternatively or additionally, radial search machine-learning process 156 may include variants of radial search methods and algorithms such as k-nearest neighbors, approximate nearest neighbors, fixed-radius near neighbors, and all nearest neighbors.

Continuing in reference to FIG. 1, providing the representation of the predicted alimentary element and the alternative alimentary element may include generating, using the predictive machine-learning process 132, a user-indicated alimentary element log, wherein the predictive machine-learning process includes selections of alimentary elements in the user-indicated alimentary element log in real-time. As used in this disclosure, a "user-indicated alimentary element log" is a cache, log, file, or the like, configured for saving at least a user-selected alimentary element to a database for use by system 100. As used in this disclosure, "real-time" refers to instantaneous determination by computing device 104 as soon as data and/or input is generated as a function of user interaction. As used herein, a database may refer to any information repository suitable to storing and/or retrieving a cache of past user-selected options and/or graphical user interface inputs, including any and all associated data, for use by system 100. In non-limiting illustrative examples, a database may include a NOSQL database which employs a mechanism for storage and/or retrieval of geophysical data, order chronicle 112, patterns of ordering, patterns of user movement, alimentary elements provided to user and selected by user, user search inputs, and the like, as described in further detail below.

Continuing in reference to FIG. 1, generating, using the predictive machine-learning process 132, the user-indicated alimentary element log may include building a user-indicated alimentary element catalogue. A "user-selected alimentary element catalogue," as used herein is an order chronicle 112 that has been created through use of system 100, wherein originator geophysical data, etc. are associated with the alimentary elements the user has selected and/or has removed from a queue since initializing system 100. In non-limiting illustrative examples, a user-indicated alimentary element catalogue 160 may include a plurality of predicted alimentary elements 124 a user has selected and/or indicated not to have ordered despite being provided, including originators, and geophysical locations of radial searches and solutions that have worked.

Continuing in reference to FIG. 1, logging user-selected option may include generating, using the alimentary machine-learning model 120, at least a predicted biological extraction datum of the user as a function of the user-indicated alimentary element catalogue. updating, using the alimentary machine-learning model 120, the biological extraction 108 of the user as a function of the user-indicated alimentary element catalogue 160. Alimentary machine-learning model 120 may be trained, as described above, for relationships between order chronicle 112 and biological extraction, and system 100 may include all user-selected options cached from system 100 to iteratively generate predicted biological extraction 164. "Predicted biological extraction," as used in this disclosure, is an element of biological extraction data relating to a user that is output by system 100 according to selected alimentary elements without being directly observed. Predicted biological extraction 164 is an element of data that is predicted by a machine-learning model trained with data that relates user-indicated alimentary elements to the user's current biological extraction. Predicted biological extraction 164 may be stored and/or retrieved using a database. Predicted biological extraction 164 may be provided to a user via a graphical user interface. Predicted biological extraction 164 may include predicted effects and/or parameters pertaining to a user according to any changes in ordering behaviors and/or patterns. In non-limiting illustrative examples, predicted biological extraction 164 may include calculated differences in nutrition, including calories, macronutrients, potential nutritional deficiencies, and the like, wherein a user has been ordering alimentary elements with fewer calories fewer alimentary element orders per day. In further non-limiting illustrative examples, predicted biological extraction 164 may include information regarding sodium intake as it relates to user blood pressure, wherein a graphical user interface provides sodium intake versus daily recommended intake and blood pressure as a function of time.

Figure 2:
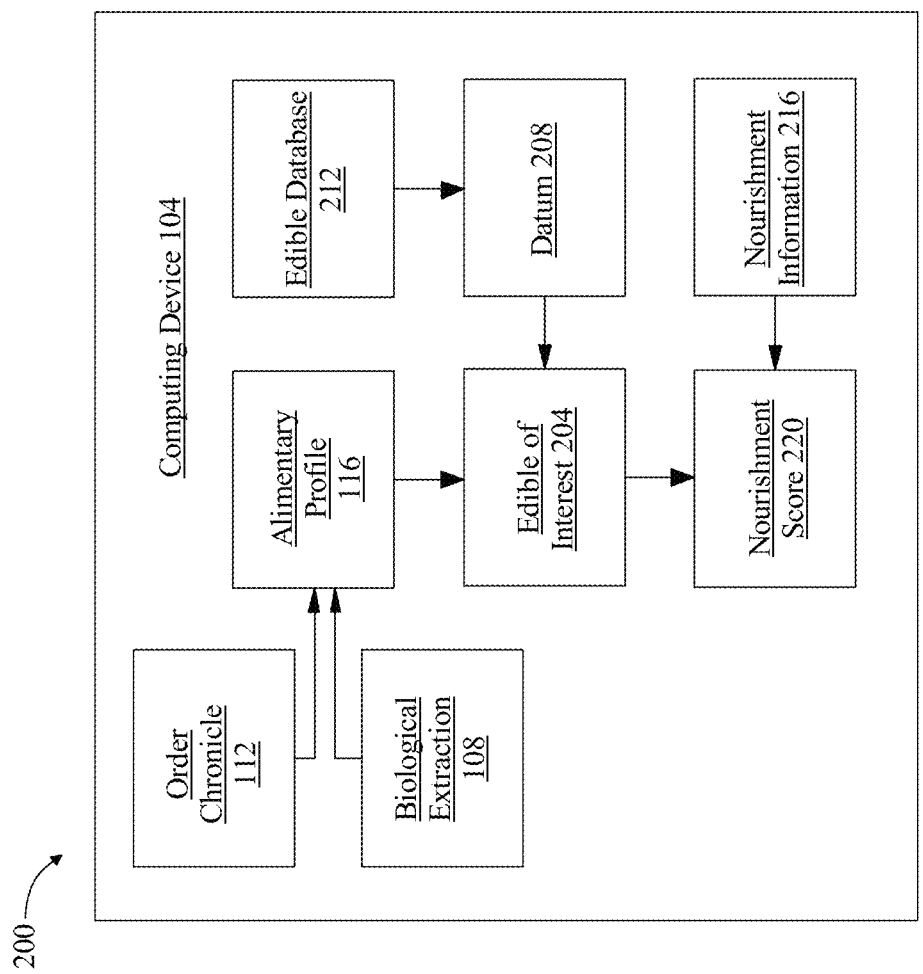
FIG. 2 is a block diagram illustrating an exemplary embodiment of a system for generating a nourishment score.

Now referring to FIG. 2, a system 200 for generating a nourishment score is illustrated. System 200 includes a computing device 104. Computing device 104 may include any computing device 104 as described above in reference to FIG. 1. In an embodiment, and without limitation, computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing in reference to FIG. 2, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 2, computing device 104 is configured to identify an alimentary profile 116. Alimentary profile 116 may include any alimentary profile 116 as described above in reference to FIG. 1. For example, and without limitation, alimentary profile may include a profile that indicates a user has a plurality of allergies and/or intolerances. As a further non-limiting example, alimentary profile 116 may include a profile denoting one or more relationships that indicate a user habit user history, alimentary element patterns, and the like there of. In an embodiment, and without limitation, identifying alimentary profile 116 may include determining a user ordering behavior. As used in this disclosure a "user ordering behavior" is a behavior and/or routine that a user exhibits when ordering an edible and/or aliment. For example, and without limitation, user ordering behavior may denote that a user routinely and/or habitually orders pizza every Friday. As a further non-limiting example, user ordering behavior may denote that a user routinely and/or habitually avoids dairy products. Computing device 104 may identify alimentary profile 116 as a function of user ordering behavior. For example, computing device 104 may identify an alimentary profile of a vegan as a function of a user ordering behavior denoting a user routinely avoids meat and/or dairy products.

Still referring to FIG. 2, computing device 104 is configured to identify alimentary profile as a function of obtaining a biological extraction 108. Biological extraction 108 may include any biological extraction 108 as described above in reference to FIG. 1. For example, and without limitation, biological extraction 108 may include medical histories, diseases, surgeries, injuries, symptoms, exercise frequency, sleep patterns, lifestyle habits, and the like, that may be used to inform a user's diet. As a further non-limiting example, biological extraction 108 data may include diet information such as nutrition deficiencies, food intolerances, allergies, and the like. As a further non-limiting example, biological extraction 108 data may alternatively or additionally include a plurality of dimensions of biological extraction 108 data any data used as a biological extraction as described in U.S. Nonprovisional application Ser. No. 16/886,647, the entirety of which is incorporated herein by reference. Computing device 104 determines an alimentary order chronicle 112 of a user. Order chronicle 112 includes any of the order chronicle 112 as described above, in reference to FIG. 1. In an embodiment, and without limitation, order chronicle 112 may include all alimentary elements a user may have ordered via a mobile app, web-browser, in-person, via phone, or any other method, for take-out, dine-in, and/or delivery. In another embodiment, and without limitation, order chronicle 112 may include all alimentary elements a user may have obtained at a grocery store. In another embodiment, and without limitation, order chronicle 112 may include a chronological history wherein the dates and times of alimentary elements a user has ordered and/or otherwise obtained is included in the order chronicle.

Still referring to FIG. 2, computing device 104 may be configured to retrieve a performance profile 112. As used in this disclosure a "performance profile" is a profile representing a biological performance of a user's body, wherein a biological performance is an efficiency of a process and/or function of a biological system. In an embodiment, and without limitation, performance profile may represent a plurality of biological performances relating to a user's stress level, such as information describing how often a user feels stressed in an average week, how much stress on average a user feels over a specified period of time, triggers of stress for the user, stress coping mechanisms, and the like. In an embodiment, and without limitation, performance profile may specify that a user feels extremely stressed out before presentations, but that deep breathing exercises help mitigate feelings of stress for the user. In an embodiment, and without limitation, performance profile may specify that a user feels most stressed out at the beginning of the week when the user has a lot of items to complete, and the user feels less stressed out as the week progresses, and the user starts to complete certain items. In an embodiment, and without limitation, performance profile may represent a plurality of biological performances relating to a user's toxicity level. A toxicity level may include any information describing a degree to which a substance and/or any mixture of one or more substances has damaged a user's body. A toxicity level may contain one or more indicators of substances that include, but are not limited to heavy metals, solvents, volatile organic compounds, pesticides, bisphenol A, phthalates, parabens, electromagnetic field radiation, heterocyclic amines, intestinal bacteria, yeast, candida, infectious disease, food additives, chemicals, glyphosate, insulin resistance, medications, stress, and/or emotions. For example, a toxicity level may include one or more measurements of heavy metals such as aluminum, antimony, arsenic, barium, beryllium, bismuth, cadmium, cesium, gadolinium, lead, mercury, nickel, palladium, platinum, tellurium, thallium, thorium, tin, tungsten, uranium, and the like. Performance profile may include information relating to a user's emotional and/or psychological state, including one or more indicators of age, sex, financial well-being, sedentary lifestyle, career stress, personal relationships, significant life events such as a death in the family or a divorce, unresolved emotional trauma, post-traumatic stress disorder, and the like. In an embodiment, and without limitation, information relating to a performance profile may be stored within a user database. User database may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 2, performance profile may be obtained as a function of a questionnaire. A "questionnaire," as used in this disclosure, is an instrument containing one or more prompts for information from a participant such as a user. A questionnaire may include one or more questions prompting a user to respond to a request to obtain information relating to a performance profile and/or alimentary profile 116. In an embodiment, computing device 104 may display a questionnaire within a display interface. A questionnaire may include one or more question styles and/or types of questions including but not limited to true or false questions, multiple choice questions, ordering questions, open ended essay questions, fill in the blank questions, matching questions, and the like. For example, a questionnaire may include a question asking a user to describe the user's sleeping habits over the course of the previous night. One or more answers to a questionnaire may be obtained from a user client device, operated by a user. A user client device may include without limitation, an additional computing device such as a mobile device, laptop, desktop computer, and the like. A user client device may include, without limitation, a display in communication with computing device 104.

In an embodiment, and still referring to FIG. 2, performance profile may be obtained from sensor data. Sensor data may be obtained from any sensor and/or medical device configured to capture sensor data concerning a user, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmography equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. A wearable and/or mobile device sensor may capture step, gait, and/or other mobility data, as well as data describing activity levels and/or physical fitness. A wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

Still referring to FIG. 2, computing device 104 is configured to determine an edible of interest 204. As used in this disclosure an "edible of interest" is any edible that computing device 104 selects to present to a user within a display interface, as a possible item that a user may be interested in and/or may wish to consume, wherein an "edible," as used herein, is any substance consumed by a human being. In an embodiment, and without limitation, edible may include a single ingredient, a combination of one or more ingredients, a meal including breakfast, lunch, dinner, snack, dessert, beverage, and/or any combination thereof. For instance and without limitation, edible may include a breakfast option such as buckwheat pancakes topped with fresh berries and raw honey. In yet another non-limiting example, an edible may include a beverage such as ginger lime kombucha. In an embodiment, and without limitation, edible of interest 204 may be identified based on information relating to a user's dietary habits. A "dietary habit," as used in this disclosure, is data including any character, numerical, and/or symbolic data representing a user's eating patterns. A dietary habit may include information relating to a user's food preferences, style of eating, food likes, food dislikes, mealtimes, average number of meals consumed each day, and the like. For instance and without limitation, a dietary habit may specify that a user consumes two meals per day, with a first meal generally around 1 PM, and a second meal around 6 PM. In yet another non-limiting example, a dietary habit may specify that a user follows a vegan diet for breakfast and lunch but consumes seafood at dinner. In yet another non-limiting example, a dietary habit may specify that a user dislikes asparagus, and the user abstains from eating asparagus. Information relating to a user's dietary habits may be stored within a database. For example, information may be stored in a database such that a user's dietary habits may be retrieved as a function of a previously identified dietary habit that has been stored in the database.

With continued reference to FIG. 2, computing device 104 may receive a datum 208 as a function of an edible database. As used in this disclosure a "datum" is any information pertaining to an edible that assists in determining an edible of interest. For example, and without limitation, datum 208 may denote one or more qualities, availabilities, concentrations, and the like there of an edible. In an embodiment and without limitation, datum 208 may be stored within edible database 212. Edible database 212 may be implemented as any data structure suitable for use as user database 212. One or more tables contained within edible database 212 may include a machine learning table; edible machine learning table may include information relating to a machine-learning process. One or more tables contained within edible database 212 may include edible training data table; edible training data table may include information relating to one or more training sets associated to an edible. One or more tables contained within edible database 212 may include an edible table; edible table may include information relating to one or more edibles. One or more tables contained within edible database 212 may include an edible provider table; edible provider table may include information relating to one or more edible providers, such as a meal maker. One or more tables contained within edible database 212 may include a caloric input table; caloric input table may include information relating to the caloric input of one or more edibles, wherein caloric input is described below. One or more tables contained within edible database 128 may include a nutrient table; nutrient table may include information relating to the nutrient input of one or more edibles, wherein nutrient input is described below. One or more tables contained within edible database 128 may include a nutritional impact; nutritional impact may include information relating to the nutritional impact of one or more edibles, wherein nutritional impact is described below.

In an embodiment, and still referring to FIG. 2, computing device 104 may determine an edible of interest as a function of an element of user geolocation data. An "element of user geolocation data," as used in this disclosure, is an element of data representing a real-world geographical location of a user. In an embodiment, and without limitation, an element of user geolocation data may include a global positioning system (GPS) of a user, and/or geographic coordinates that specify the latitude and longitude of particular location where a user is located. In another embodiment, and without limitation, an element of user geolocation data may be obtained from a radar source, user client device, self-reported by the user, and the like. Computing device 104 may receive an element of user geolocation data and identify a plurality of edibles as a function of the element of user geolocation data. Additionally or alternatively, computing device 104 may generate a query, to search for edibles that may be available within the user's geolocation. A "query," as used in this disclosure, is any search term used to retrieve information relating to an edible, from a database, such as edible database 212. For instance and without limitation, computing device 104 may utilize a user's geolocation that specifies a user is located in Anchorage, Alaska to generate a query containing "Anchorage, Alaska" to identify a plurality of edibles available within Anchorage, Alaska. Computing device 104 displays a plurality of edibles within a display interface and receives a user selection containing an edible of interest, wherein a display interface is described below. A user selection may include any user choice, picking one or more edibles from within a plurality of edibles. A user selection may be received from user client device such as but not limited to a mobile phone, tablet, laptop, computing device, television, and the like thereof. Computing device is configured to determine edible of interest 204 as a function of alimentary profile 116 and datum 208, wherein determining may include any of the determining as described above, in reference to FIG. 1.

Still referring to FIG. 2, computing device 104 is configured to obtain a nourishment information 216. As used in this disclosure a "nourishment information" is data, including any numerical, character, and/or symbolic data, describing the nutritional content of edible of interest 204. Nourishment information 216, may include information describing the contents and/or ingredients of an edible and/or the impact of an edible of interest 204 on a human body. Nourishment information 204 may include a caloric input, describing the total calorie count contained within an edible of interest 204. As used in this disclosure a "caloric input" is an element of data representing one or more calories and/or energy sources of an edible. For example, and without limitation, caloric input may represent that an edible of interest includes 1200 kcals. In an embodiment, and without limitation, nourishment information 216 may include a nutrient input. As used in this disclosure a "nutrient input" is an element of data representing the total quantities of one or more nutrients contained within an edible. For example, a nutrient input may describe the total number of carbohydrates, fats, proteins, minerals, additives, enzymes, vitamins, sugar, cholesterol, and the like contained within a specified serving of an edible. In another embodiment, and without limitation, nourishment information 216 may include a nutritional impact. As used in this disclosure a "nutritional impact" is a proposed and/or predicted nutritional effect an edible has based on the edible composition. For example, and without limitation, nutritional impact may include raising blood glucose level as a function of an edible comprising 4 g of carbohydrates. In an embodiment, and without limitation, nourishment information 216 may specify that an edible containing a dinner option containing chicken parmesan with baked ziti contains 1200 calories in a serving size that equates to half of the dinner option. In yet another non-limiting example, nourishment information 216 may specify that a salad containing tuna fish and avocado in a green goddess dressing contains 400 calories in the entire salad, and contains 16 grams of fat, 20 grams of protein, 10 grams of carbohydrates, 6 grams of sugar, and 6 grams of fiber. Nourishment information 216 may be obtained from third party device and stored within edible database 212. Third party device may include any device suitable for use as user client device, as described above. An entry containing nourishment information 216 may be generated by a meal maker who prepares and/or cooks an edible, one or more experts in the field of nutrition and nourishment such as scientists, dieticians, nutritionists, researchers, clinicians, medical professionals and the like. Information relating to nourishment information 216 may be updated in real time, using any network methodology as described herein. Information pertaining to nourishment information 216 may be stored within edible database 212.

With continued reference to FIG. 2, computing device 104 may be configured to obtain nourishment information 216 as a function of a dietary classifier. A "classifier," as used in this disclosure, is a process in which computing device 104 sorts inputs into categories or bins of data. A classifier may be generated using a classification process, including a classification algorithm. Classification may be performed using any of the classification processes and/or classification algorithms as described in U.S. Nonprovisional application Ser. No. 16/699,616 filed on Nov. 30, 2019, and entitled "METHODS AND SYSTEMS FOR INFORMING FOOD ELEMENT DECISIONS IN THE ACQUISITION OF EDIBLE MATERIALS FROM ANY SOURCE," the entirety of which is incorporated herein by reference. A "dietary classifier," as used in this disclosure, is a classifier that uses an edible of interest as an input and outputs, a dietary label using a classification process. A "dietary label," as used in this disclosure, identifies one or more dietary patterns and/or ways of eating that an edible may fulfill. For example, a dietary label may indicate that an edible containing quinoa linguine cooked with olive oil, basil and tomatoes and topped with shrimp fulfills a Mediterranean diet, a gluten free diet, a dairy free diet, a pescatarian diet, and the like. Dietary classifier may be trained using training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data may be obtained from expert inputs, previous iterations of generating a classification process, and the like.

Still referring to FIG. 2, computing device 104 is configured to generate a nourishment score 220 as a function of edible of interest 204 and nourishment information 216. As used in this disclosure a "nourishment score" is an element of data, including any character, symbolic, and/or numerical data, containing a score reflecting an optimal combination of the nourishment and/or qualities necessary for growth, health and/or good condition of an edible on a user's body and/or health and a likelihood of the user to consume the edible. Nourishment score 220 may be transient and/or dynamic. Nourishment score 220 may be graded on a continuum, where a score of zero may indicate an edible that will have extremely poor nourishment on a user, while a score of 100 may indicate an edible that will have excellent nourishment on a user. An edible score may be updated based on a serving size of an edible.

In an embodiment, and without limitation, computing device 104 may calculate nourishment score 220 as a function of a score machine-learning model. As used in this disclosure "score machine-learning model" is a machine-learning model to produce a nourishment score output given nourishment information and/or alimentary profiles as inputs; this is in contrast to a non-machine learning software program where the commands to be executed are determined in advance by a user and written in a programming language. Score machine-learning model may include one or more score machine-learning processes such as supervised, unsupervised, or reinforcement machine-learning processes that computing device 104 and/or a remote device may or may not use in the determination of nourishment score 220. As used in this disclosure "remote device" is an external device to computing device 104. Score machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 2, computing device 104 may train score machine-learning process as a function of a score training set. As used in this disclosure a "score training set" is a training set that correlates a nourishment information and/or alimentary profile to a nourishment score. For example, and without limitation, a nourishment information of 850 kcals and an alimentary profile of a severe malnourishment may relate to a nourishment score of 56 for increasing nourishment. The score training set may be received as a function of user-entered valuations of nourishment information, alimentary profiles, and/or nourishment scores. Computing device 104 may receive score training set by receiving correlations of nourishment information, and/or alimentary profiles that were previously received and/or determined during a previous iteration of determining nourishment scores. The score training set may be received by one or more remote devices that at least correlate a nourishment information and/or alimentary profile to a nourishment score. The score training set may be received in the form of one or more user-entered correlations of a nourishment information and/or alimentary profile to a nourishment score.

Still referring to FIG. 2, computing device 104 may receive score machine-learning model from a remote device that utilizes one or more score machine learning processes, wherein a remote device is described above in detail. For example, and without limitation, a remote device may include a computing device, external device, processor, and the like thereof. Remote device may perform the score machine-learning process using the score training set to generate nourishment score 220 and transmit the output to computing device 104. Remote device may transmit a signal, bit, datum, or parameter to computing device 104 that at least relates to nourishment score 220. Additionally or alternatively, the remote device may provide an updated machine-learning model. For example, and without limitation, an updated machine-learning model may be comprised of a firmware update, a software update, a score machine-learning process correction, and the like thereof. As a non-limiting example a software update may incorporate a new nourishment information that relates to a modified alimentary profile. Additionally or alternatively, the updated machine learning model may be transmitted to the remote device, wherein the remote device may replace the score machine-learning model with the updated machine-learning model and determine the nourishment score as a function of the nourishment information using the updated machine-learning model. The updated machine-learning model may be transmitted by the remote device and received by computing device 104 as a software update, firmware update, or corrected score machine-learning model. For example, and without limitation score machine-learning model may utilize a random forest machine-learning process, wherein the updated machine-learning model may incorporate a gradient boosting machine-learning process.

Still referring to FIG. 2, computing device 104 may determine nourishment score 220 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In an embodiment, and without limitation, classifier may classify an edible to a set of edibles that have previously identified nourishment scores, wherein the classifier may determine a nourishment score for the edible as a function of the set of edibles. In another embodiment, and without limitation, classifier may classify an edible to an edible group, wherein the edible group may be used to determine a nourishment score as a function of the edible group. For example, an edible of a kale may be classified to an edible group of fiber, wherein the edible group may have a score of 35.

Still referring to FIG. 2, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 2, computing device 104 may be configured to initiate a display interface within the computing device. A "display interface," as used in this disclosure, is a user interface that allows a user to interface with computing device 104 through graphical icons, audio indicators, command labels, text navigation and the like. Display interface may include a form or other graphical element having display fields, where one or more elements of information may be displayed. Display interface may include slides or other user commands that may allow a user to select one or more characters. Display interface may include free form textual entries, where a user may type in responses and/or messages. Display interface may display data output fields including text, images, or the like. Display interface may include data input fields such as text entry windows, drop-down lists, buttons, checkboxes, radio buttons, sliders, links, or any other data input interface that may capture user interaction as may occur to persons skilled in the art upon reviewing the entirety of this disclosure. Display interface may be provided, without limitation, using a web browser, a native application, a mobile application, or the like. In an embodiment, and without limitation, computing device 104 may be configured to calculate a first nourishment score 220 for a first edible of interest 204, calculate a second nourishment score 220 for a second edible of interest 204, and chart the first nourishment score 220 as a function of the second nourishment score 220. Charting may include mapping and/or graphing a first nourishment score 220 as compared to a second nourishment score 220. For instance and without limitation, a first edible of interest 204 that contains a first nourishment score 220 of 74 for a first edible of interest 204 containing grilled salmon served with rice pilaf and steamed broccoli may be charted on a graph versus a second edible of interest 204 that contains a second nourishment score 220 of 22 for a second edible of interest 204 containing fried chicken served with mashed potatoes and gravy. A chart may be displayed within display interface for a user to view a first nourishment score charted as a function of a second nourishment score. Nourishment score 220 data may alternatively or additionally include a plurality of nourishment scores used as a nourishment score as described in U.S. Nonprovisional application Ser. No. 16/983,034, filed on Dec. 28, 2020, and entitled "METHODS AND SYSTEMS FOR CALCULATING AN EDIBLE SCORE IN A DISPLAY INTERFACE," the entirety of which is incorporated herein by reference.

Figure 3B:
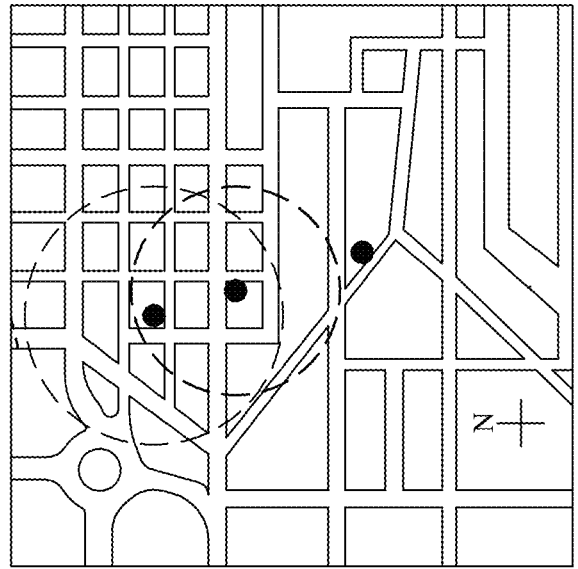
FIGS. 3A-3B is a diagrammatic representation of a non-limiting exemplary embodiment of radial search for locating alimentary element.
Figure 3A:
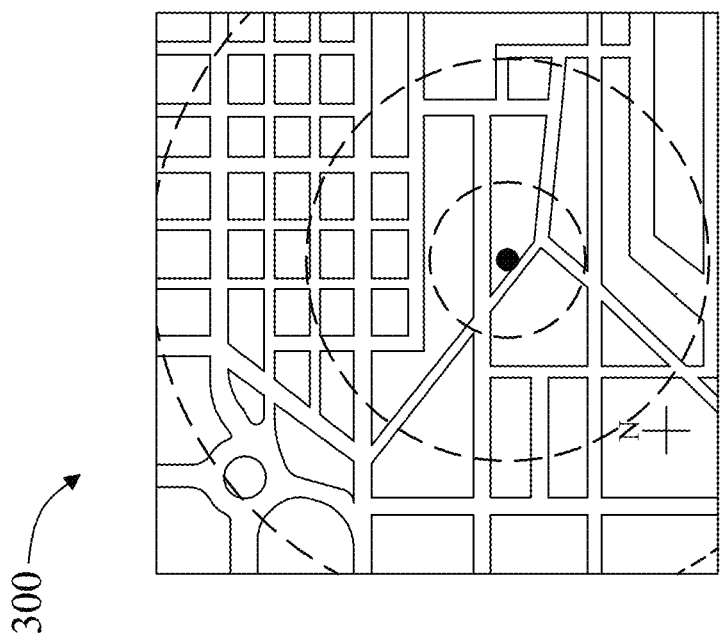

Referring now to FIG. 3A and FIG. 3B, an exemplary embodiment 300 of radial search for locating alimentary element originators is illustrated. Computing device 104 may use radial search machine-learning process 156 to locate alimentary element originators within a first radius. As depicted in FIG. 3A, radial search may select a first search radius to search based on a user location (black-shaded circle), wherein a first circle (dashed line) of area about the user is searched for a suitable originator. In the event that a suitable originator is not located, the radius may widen to larger radii concentric rings (larger dashed-line rings). Alternatively or additionally, as depicted in FIG. 3B, a first radius may be searched about a first local solution that is a first alimentary element originator (black-shaded circle) until a better solution is located (grey-shaded circle), and in the even the alimentary originator is not suitable, or the user indicates a different alimentary element, or the solution is otherwise not optimal, a second radius may be searched, which may locate additional originators (white circle). Each additional search radii may be larger or smaller than a previous search radius but may include a different search center.

Figure 4:
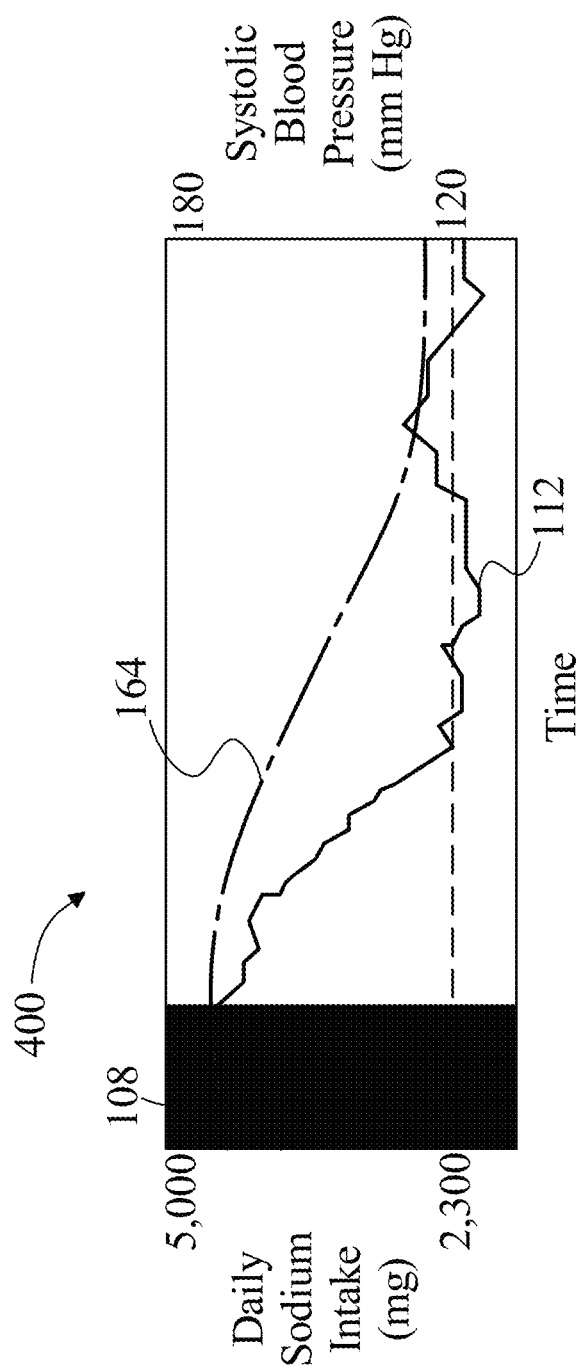
FIG. 4 is a diagrammatic representation of a non-limiting exemplary embodiment of biological extraction as a function of order chronicle.

Referring now to FIG. 4, a non-limiting exemplary embodiment 400 of predicted biological extraction 164 as a function of user order chronicle 112 is illustrated. User order chronicle 112 daily sodium intake from logged alimentary elements a user has ordered as a function of time is shown as a solid black line (graphed to left y-axis) about a daily recommended threshold of 2,300 mg sodium (depicted as dashed line at y=2,300 mg). System 100 may provide alternative alimentary elements 128 based on user order chronicle 112 with the intended effect of reducing daily sodium intake toward the daily recommended threshold to reduce blood pressure, wherein as a function of time a user may order alternative alimentary element 128 in place of alimentary elements more like temporally anterior alimentary elements. Systolic blood pressure (in mm Hg) of a user is depicted as a chain-dashed curve (graphed to right y-axis) as a function of time. System may determine a user's systolic blood pressure as a function of their order chronicle over time (for instance as over a several months-long period) and provide the predicted biological extraction 164 as a function of the order chronicle 112. In FIG. 4, biological extraction 108 and order chronicle 112 in the grey shaded region of the graph (leftmost portion) may represent data generated prior to a user began using system 100, including temporally anterior alimentary elements' sodium content and past user systolic blood pressure data. Biological extraction 164 to the right of the grey shaded region represents updated data points that are predicted from the order chronicle 112 that has been logged since user began using system 100. System 100 may use machine-learning processes, described herein, to determine how order chronicle 112 patterns, for instance sodium intake in milligrams (mg), may affect biological extraction parameters, for instance systolic blood pressure in millimeters mercury (mm Hg). Such relationships may be stored and/or retrieved from a database and used to inform further determinations by system 100, including predicted alimentary elements 124, alternative alimentary elements 128, originator locations, and the like.

Figure 5:
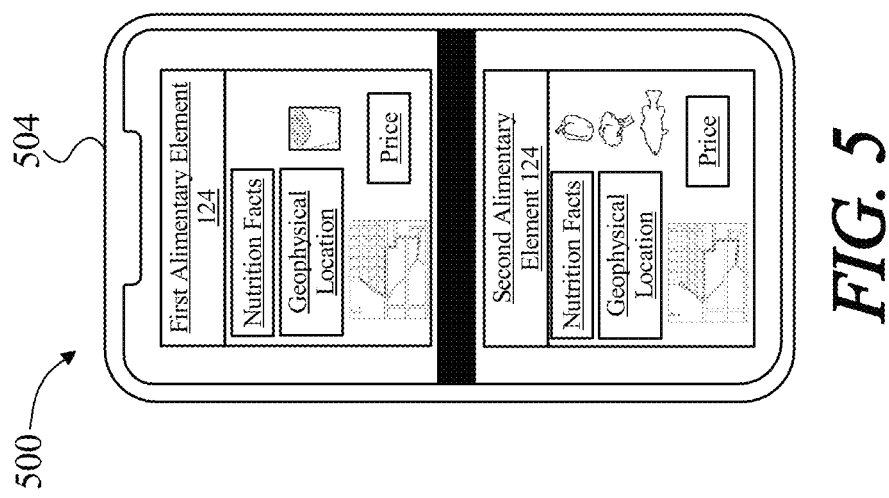
FIG. 5 is a diagrammatic representation of a non-limiting exemplary embodiment of a user device.

Referring now to FIG. 5, a non-limiting exemplary embodiment 500 of a user device generating a representation of a predicted alimentary element 124 and an alternative alimentary element 128. User device 504 may include a computing device 104. User device 504 may include a "smartphone", laptop, computer, tablet, internet-of-things (IOT) device, or the like, that is capable of performing system 100, as described herein. User device 504 may generate a representation of a predicted alimentary element 124, including any associated alimentary metrics, for instance and without limitation, the identity of an alimentary element originator, the geophysical location, nutrition facts, price, etc. In exemplary embodiments, user device 504 may use a mapping application or algorithm, for instance and without limitation, a web-based navigation application such, a mobile navigation application, or the like, that may communicate to a user a route for pick-up, take-out, dine-in, and the like, from ordering and/or obtaining an alimentary element.

Figure 6:
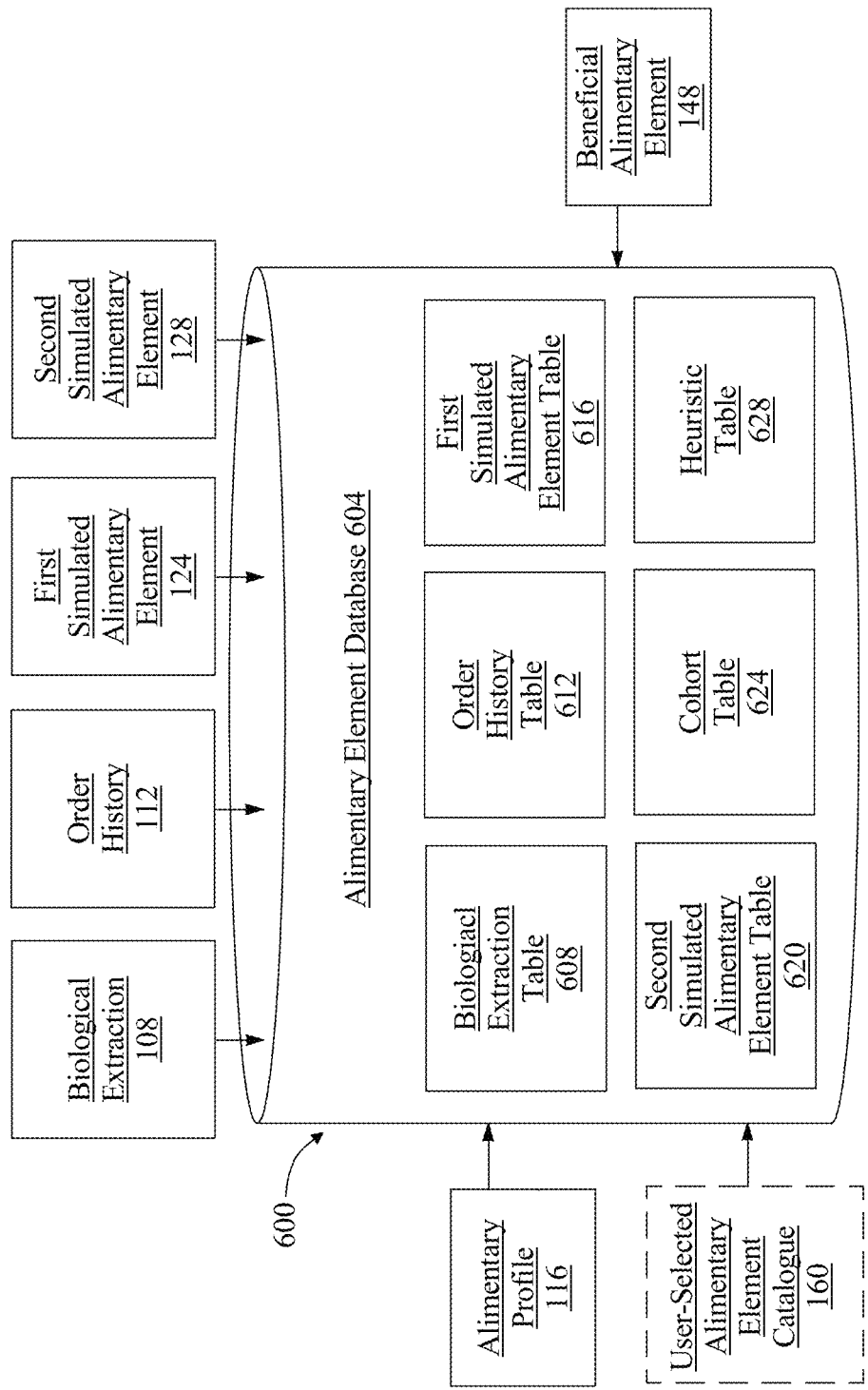
FIG. 6 is a block diagram illustrating a non-limiting exemplary embodiment of an alimentary element database.

Referring now to FIG. 6, a non-limiting exemplary embodiment 600 of an alimentary element database 604 is illustrated. Alimentary element database 604 may be implemented, without limitation, as a relational database, a key-value retrieval database such as a NOSQL database, or any other format or structure for use as a database that a person skilled in the art would recognize as suitable upon review of the entirety of this disclosure. Alimentary element database 604 may alternatively or additionally be implemented using a distributed data storage protocol and/or data structure, such as a distributed hash table and the like. Alimentary element database 604 may include a plurality of data entries and/or records, as described above. Data entries in an alimentary element database 604 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 6, alimentary element database 604 may include, without limitation, a biological extraction table 608, order chronicle table 612, predicted alimentary element table 616, alternative alimentary element table 620, cohort table 624, and/or heuristic table 628. Determinations by a machine-learning process, machine-learning model, ranking function, and/or mapping algorithm, may also be stored and/or retrieved from the alimentary element database 604, for instance in non-limiting examples a classifier describing a plurality of alimentary elements as it relates to an order chronicle 112, wherein a classifier is an identifier that denotes a subset of data that contains a heuristic and/or relationship, as may be useful to system 100 described herein. Determinations by a machine-learning process for selecting a region for determining an alimentary element originator and/or any associated, geophysical data, nutrition facts, item lists, prices, and the like, may also be stored and/or retrieved from the alimentary element database 604. As a non-limiting example, alimentary element database 604 may organize data according to one or more instruction tables. One or more alimentary element database 604 tables may be linked to one another by, for instance in a non-limiting example, common column values. For instance, a common column between two tables of alimentary element database 604 may include an identifier of a submission, such as a form entry, textual submission, global position system (GPS) coordinates, addresses, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Still referring to FIG. 6, in a non-limiting embodiment, one or more tables of an alimentary element database 604 may include, as a non-limiting example, a biological extraction table 608, which may include categorized biological extraction data, as described above, including biological, physiological, chemical, etc., data. One or more tables may include order chronicle table 612, which may include a history of numerical values, GPS coordinates, addresses, timestamps, alimentary elements, and the like, for instance and without limitation, that system 100 may use to retrieve and/or store nutrition facts, prices, ingredient lists, and the like, associated with user order chronicle 112. One or more tables may include a predicted alimentary element table 616, which may store and/or organize the number and identity of alimentary elements, their nutrition facts, geolocation, price, and the like. One or more tables may include an alternative alimentary element table 620, which may store and/or organize the number and identity of alimentary elements, their nutrition facts, geolocation, price, and the like. One of more tables may include a cohort table 624, which may include user data from a plurality of users, organized into subsets of data, for instance and without limitation, using classifiers generated by classification machine-learning processes and/or algorithms. One or more tables may include, without limitation, a heuristic table 628, which may organize rankings, scores, models, outcomes, functions, numerical values, vectors, matrices, and the like, that represent determinations, optimizations, iterations, variables, and the like, include one or more inputs describing potential mathematical relationships between at least an element of user data and, for instance and without limitation, predicted alimentary elements, predicted biological extraction 164, and the like, as described herein.

Figure 7:
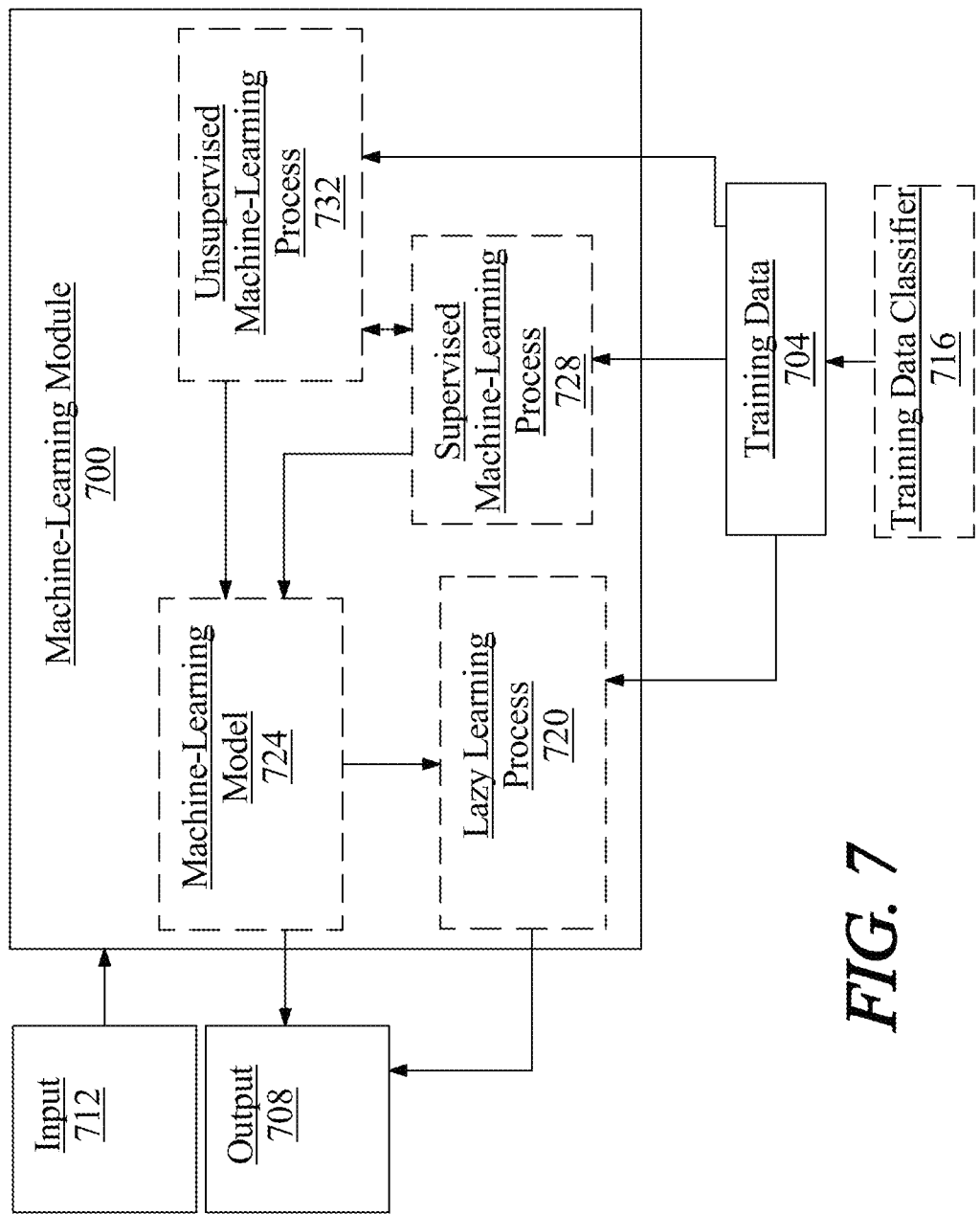
FIG. 7 is a block diagram illustrating a non-limiting exemplary embodiment of a machine-learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail herein. Training data 704 used by machine-learning module 700 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail herein; such models may include without limitation a training data classifier 716. Training data classifier 716 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a process whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to elements that characterizes a sub-population, such as a subset of physical transfer paths and/or other analyzed items and/or phenomena for which a subset of training data may be selected.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a plurality of predicted alimentary elements 124 and biological extraction 108 as described above as inputs, candidate alternative alimentary elements 128 as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 7, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 704.

Figure 8:
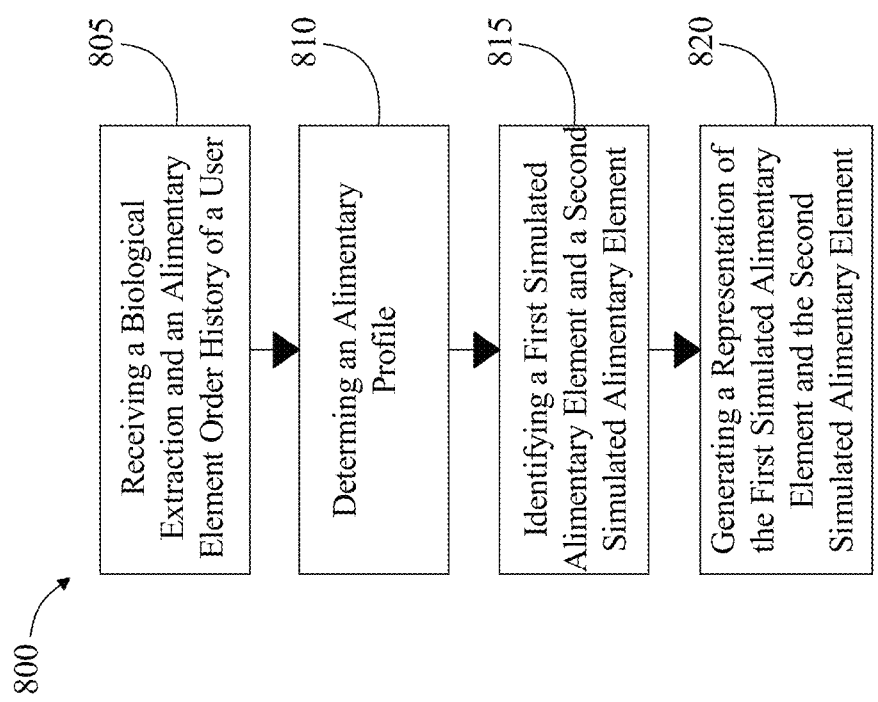
FIG. 8 is a flow diagram illustrating an exemplary workflow of a method for predicting alimentary element ordering based on biological extraction.

Referring now to FIG. 8, an exemplary embodiment of a method 800 for predicting alimentary element ordering based on biological extraction. At step 805, computing device 104 is configured for receiving a biological extraction 108 of a user and an alimentary element order chronicle 112 of a user. Receiving, by the computing device 104, the alimentary element order chronicle 112 may include generating training data using the alimentary element order chronical 112 to train the alimentary machine-learning model 120 for user alimentary element patterns; this may be implemented, without limitation, as described above in reference to FIGS. 1-7.

Continuing in reference to FIG. 8, at step 810, computing device 104 is configured for determining an alimentary profile 116, wherein determining the alimentary profile 116 includes training an alimentary machine-learning model 120 with training data that includes a plurality of entries wherein each entry relates user biological extraction 108 to alimentary element order chronicle, and generating the alimentary profile 116 as a function of the alimentary machine-learning model 120. Generating the alimentary machine-learning model 120 may include training a model to find at least a mathematical relationship between user alimentary element patterns and user biological extraction 108 data, wherein the mathematical relationship describes how user alimentary element patterns affect user biological extraction parameters; this may be implemented, without limitation, as described above in reference to FIGS. 1-7.

Continuing in reference to FIG. 8, at step 815, computing device 104 is configured for identifying, using the alimentary profile 116 and a predictive machine-learning process 132, a predicted alimentary element 124 and an alternative alimentary element 128, wherein generating includes determining, using the predictive machine-learning process 132 and the alimentary profile 116, the predicted alimentary element 124, wherein the predicted alimentary element 124 is a predictive alimentary element a user is expected to order, and generating, using the predicted alimentary element 124, the alternative alimentary element 128, wherein generating includes creating a classifier, using a classification machine-learning process, wherein the classifier contains alimentary element metrics of the predicted alimentary element 124, and ranking alimentary elements as a function of effect to a user's biological extraction 108 if substituted for the predicted alimentary element 124. Generating the predicted alimentary element 124 may include searching, using the alimentary profile 116 and the predictive machine-learning process 132, for a plurality of alimentary elements, wherein searching may include identifying alimentary element metrics present in the temporally anterior alimentary element, and locating the plurality of alimentary elements containing similar alimentary element metrics, calculating, using the alimentary element metrics, a first similarity metric 136 between the temporally anterior alimentary element and each of the plurality of alimentary elements, ranking, using a ranking machine-learning process 140, the plurality of alimentary elements based on the first similarity metrics 136, and selecting the predicted alimentary element 124 based on the ranking of the plurality of alimentary elements. Generating the alternative alimentary element 128 may include generating a sustenance machine-learning model 144, wherein the sustenance machine-learning model 144 is trained with training data that includes a plurality of entries wherein each entry relates user biological extraction 108 to alimentary elements that have beneficial effects on user biological extraction 108 parameters, searching, using the sustenance machine-learning model 144, for a plurality of beneficial alimentary elements 148, retrieving alimentary element metrics of the plurality of beneficial alimentary elements 148, calculating a second similarity metric 128 based on similarity of the alimentary element metrics of the plurality of beneficial alimentary elements 148 and the predicted alimentary element 124, ranking, using the ranking machine-learning process 140, the plurality of beneficial alimentary elements 148 based on the second similarity metric 152, and selecting the alternative alimentary element 128 based on the ranking, wherein the alternative alimentary element 128 is selected from the plurality of beneficial alimentary elements 148; this may be implemented, without limitation, as described above in reference to FIGS. 1-7.

Continuing in reference to FIG. 8, at step 820, computing device 104 is configured for generating a representation via a graphical user interface of the predicted alimentary element 124 and the alternative alimentary element 128 to a user. Providing the representation of the predicted alimentary element 124 and the alternative alimentary element 128 may include queuing the predicted alimentary element 124 and the alternative alimentary element 128 with an alimentary element originator, wherein queuing includes locating a first alimentary element originator with at least a metric that matches the predicted alimentary element 124 or the alternative alimentary element 128 within a first distance of a user, and addressing a user to order an alimentary element of the predicted alimentary element 124 and the alternative alimentary element 128. Computing device 104 may generate an audiovisual notification for addressing a user to select from a plurality of alternative alimentary elements. Addressing a user to order from a plurality of alternative alimentary elements may include using a radial search machine-learning process 156, wherein the radial search machine-learning process 156 determines a first distance, and searches the first distance for an alternative alimentary element originator, wherein the user can order at least an alternative alimentary element 128 from the alternative alimentary element originator. Generating, using the predictive machine-learning process 132, a user-indicated alimentary element log, wherein the predictive machine-learning process 132 includes selections of alimentary elements in the user-indicated alimentary element log in real-time. Generating, using the predictive machine-learning process 132, a user-indicated alimentary element log may include building a user-indicated alimentary element catalogue 160 and generating, using the alimentary machine-learning model 120, at least a predicted biological extraction 164 datum of the user as a function of the user-indicated alimentary element catalogue 160; this may be implemented, without limitation, as described above in reference to FIGS. 1-7.

Figure 9:
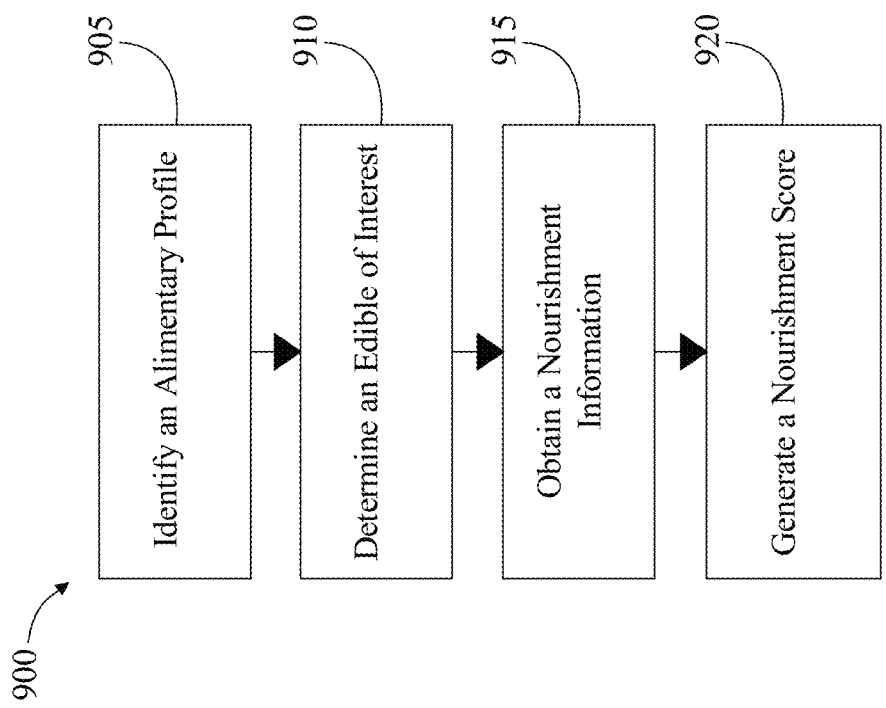
FIG. 9 is a flow diagram illustrating an exemplary workflow of a method for generating a nourishment score.

Now referring to FIG. 9, a method 900 for generating a nourishment score is illustrated. At step 905, a computing device 104 identifies an alimentary profile 116. Computing device 104 may include any of the computing device 104 as described above, in reference to FIGS. 1-8. Alimentary profile 116 may include any of the alimentary profile 116 as described above, in reference to FIGS. 1-8. Computing device 104 obtains a biological extraction 108 of a user. Biological extraction 108 may include any of the biological extraction 108 as described above, in reference to FIGS. 1-8. User may include any of the user as described above, in reference to FIGS. 1-8. Computing device 104 determines an alimentary element order chronicle 112 of a user. Order chronicle 112 may include any of the order chronicle 112 as described above, in reference to FIGS. 1-8. Computing device 104 identifies alimentary profile 116 as a function of biological extraction 108 and alimentary element order chronicle 112, wherein identifying includes any of the identifying as described above, in reference to FIGS. 1-8.

Still referring to FIG. 9, at step 910, computing device 104 determines an edible of interest 204. An edible of interest 204 may include any of the edible of interest 204 as described above, in reference to FIGS. 1-8. Computing device 104 receives a datum 208 as a function of an edible database 212. Datum 208 may include any of the datum 208 as described above, in reference to FIGS. 1-8. Edible database 212 may include any of the edible database 212 as described above, in reference to FIGS. 1-8. Computing device 104 determines edible of interest 204 as a function of alimentary profile 116 and datum 208, wherein determining may include any of the determining as described above, in reference to FIGS. 1-8.

Still referring to FIG. 9, at step 915, computing device 104 obtains a nourishment information 216 associated to edible of interest 204. Nourishment information 216 may include any of the nourishment information 216 as described above, in reference to FIGS. 1-8.

Still referring to FIG. 9, at step 920, computing device 104 generates a nourishment score 220 as a function of edible of interest 204 and nourishment information 216. Nourishment score 220 may include any of the nourishment score 220 as described above, in reference to FIGS. 1-8. Generating may include any of the generating as described above, in reference to FIGS. 1-8.

Figure 10:
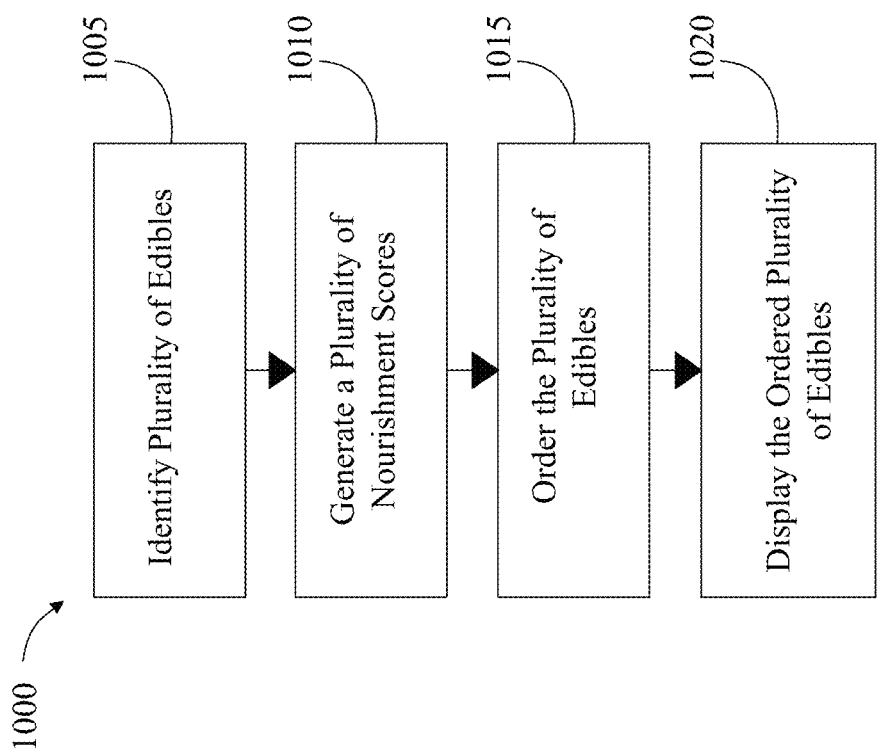
FIG. 10 is a flow diagram illustrating an exemplary method of alimentary ordering based on biological extraction.

Referring now to FIG. 10, an exemplary embodiment of a method 1000 of predicting alimentary element ordering based on biological extraction is illustrated. At step 1005, a computing device identifies a plurality of edibles; this may be implemented, without limitation, as described above in reference to FIGS. 1-9. Identifying plurality of edibles may include, as a non-limiting example, obtaining an alimentary element chronical of a user, generating an alimentary profile, as a function of the biological extraction, and identifying the plurality of alimentary elements as a function of the alimentary profile. generating alimentary profile may include receiving a biological extraction of user and generating the alimentary profile as a function of the biological extraction and alimentary element order chronical. Identifying alimentary profile may include retrieving a performance profile and generating the alimentary profile as a function of the performance profile and alimentary element order chronical.

Still referring to FIG. 10, identifying plurality of edibles may include receiving a datum as a function of an edible database and identifying the plurality of edibles as a function of alimentary profile and the datum; this may be implemented, without limitation as described above in reference to FIGS. 1-9. Identifying plurality of edibles may include receiving an element of user geolocation data and identifying plurality of edibles as a function of the alimentary profile and the element of user geolocation data.

At step 1010, and with continued reference to FIG. 10, computing device generates, for the plurality of edibles, a plurality of nourishment scores; this may be implemented, without limitation, as described above in reference to FIGS. 1-9. In an embodiment, generating plurality of nourishment scores may include generating, for each edible of the plurality of edibles, a nourishment score as a function of the edible and alimentary profile At step 1015, ordering, by the computing device, the plurality of edibles according to the plurality of nourishment scores; this may be implemented, without limitation, as described above in reference to FIGS. 1-9. Ordering may be performed, without limitation, by an ascending and/or descending numerical order of nourishment scores. Alternatively or additionally, ordering may be performed according to nourishment scores in combination with one or more additional ordering factors. One or more ordering factors may include, without limitation, any ranking as described above, and/or any data used to generate such a ranking. Additional factors may include, without limitation, a preference input, which may represent one or more preferences provided by user. For instance, and without limitation, preference input may indicate one or more ingredients, one or more flavors, one or more nutritional elements, one or more cuisines and/or styles of meals, or the like. Preference input may be provided using any user interface, graphical user interface, or other tools described above. Additional factors may include previous selections of edibles by user, updates to alimentary profile based on selections and/or other factors as described above, or the like.

Still referring to FIG. 10, computing device 104 may compute a score associated with each edible and order edibles according to the degree to which such items minimize and/or maximize the score, depending on whether an optimal result is represented, respectively, by a minimal and/or maximal score; a mathematical function, described herein as an "objective function," may be used by computing device 104 to score each possible pairing. Objective function may based on one or more objectives as described below. In various embodiments a score of a particular edible may be based on a combination of one or more factors, including nourishment score and/or any other factors described above and/or as described in this disclosure. Each factor may be assigned a score based on predetermined variables. In some embodiments, the assigned scores may be weighted or unweighted.

Continuing to refer to FIG. 10, optimization of objective function may include performing a greedy algorithm process. A "greedy algorithm" is defined as an algorithm that selects locally optimal choices, which may or may not generate a globally optimal solution. For instance, computing device 104 may select edible so that scores associated therewith are the best score for each edible.

Still referring to FIG. 10, objective function may be formulated as a linear objective function, which computing device 104 may solve using a linear program such as without limitation a mixed-integer program. A "linear program," as used in this disclosure, is a program that optimizes a linear objective function, given at least a constraint. For instance constraints may include limitation to one or more currently available edibles, one or more currently available edibles in a geographic area including user, or the like. In various embodiments, system 100 may determine an edible that maximizes a total score subject to any such constraints. A mathematical solver may be implemented to solve for edibles that maximizes score, according to which degree of solution may be used to order edibles; mathematical solver may implemented on computing device 104 and/or another device in system 100, and/or may be implemented on third-party solver.

With continued reference to FIG. 10, optimizing objective function may include minimizing a loss function, where a "loss function" is an expression an output of which an optimization algorithm minimizes to generate an optimal result. As a non-limiting example, computing device 104 may assign variables relating to a set of parameters, which may correspond to score components as described above, calculate an output of mathematical expression using the variables, and select edible that produces an output having the lowest size, and/or order in ascending order of such size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs.

At step 1020, displaying, by the computing device the ordered plurality of edibles; this may be implemented, without limitation, as described above in reference to FIGS. 1-9.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
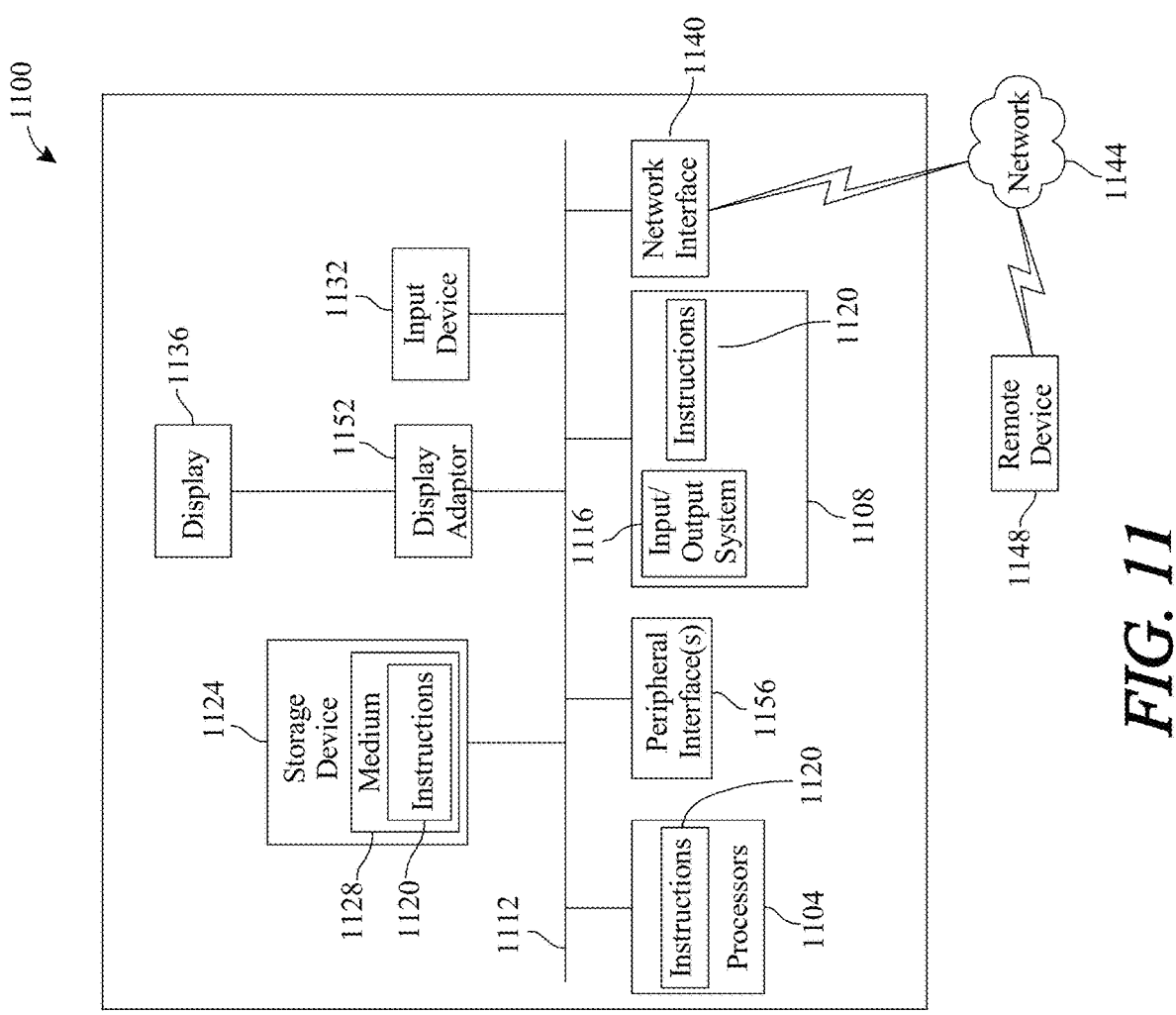
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for predicting alimentary element ordering based on biological extraction, the apparatus comprising:
at least a processor; and
a memory communicatively connected to the at least a processor, the memory containing instructions configuring the at least a processor to:
receive a plurality of biological extractions of a user;
identify a plurality of edibles, wherein identifying the plurality of edibles further comprises:
obtaining an alimentary element order chronicle of the user;
generating an alimentary profile as a function of a biological extraction of the plurality of biological extractions; and
identifying the plurality of edibles as a function of the alimentary profile;
generate, for the plurality of edibles, a plurality of nourishment scores, wherein generating the plurality of nourishment scores includes generating, for each edible of the plurality of edibles, a nourishment score as a function of the edible and the alimentary profile;
order the plurality of edibles according to the plurality of nourishment scores;
display the ordered plurality of edibles;
receive a user input comprising a user-selected option regarding the plurality of edibles;
generate a predicted biological extraction as a function of the user input, wherein generating the predicted biological extraction comprises:
training a machine-learning model on a training dataset comprising the alimentary element order chronicle and with the plurality of biological extractions; and
determining the predicted biological extraction as a function of the user input and the trained machine-learning model;
display, using a graphical user interface, the predicted biological extraction;
determine one or more alternative alimentary elements as a function of the predicted biological extraction; and
determine an alimentary element originator as a function of the one or more alternative alimentary elements using a radial search process, wherein the radial search process is based on rings, and wherein the radial search process iteratively modifies radii of the rings and generates new centers therefor to cover a search space.

2. The apparatus of claim 1, wherein generating the alimentary profile further comprises:
receiving a biological extraction of the user; and
generating the alimentary profile as a function of the biological extraction and the alimentary element order chronicle.

3. The apparatus of claim 1, wherein generating the alimentary profile further comprises:
retrieving a performance profile; and
generating the alimentary profile as a function of the performance profile and the alimentary element order chronicle.

4. The apparatus of claim 1, wherein identifying the plurality of edibles further comprises:
receiving a datum as a function of an edible database; and
identifying the plurality of edibles as a function of the alimentary profile and the datum.

5. The apparatus of claim 1, wherein identifying the plurality of edibles further comprises:
receiving an element of user geolocation data; and
identifying the plurality of edibles as a function of the alimentary profile and the element of user geolocation data.

6. The apparatus of claim 1, wherein determining each nutrition score further comprises:
receiving nourishment information regarding an edible of the plurality of edibles; and
determining the nutrition score as a function of the nourishment information.

7. The apparatus of claim 6, wherein the nourishment information comprises a caloric input.

8. The apparatus of claim 6, wherein the nourishment information comprises a nutrient input.

9. The apparatus of claim 6, wherein the nourishment information comprises a nutritional impact.

10. The apparatus of claim 1, wherein generating each nourishment score further comprises:
training a score machine-learning process using edible training data, wherein edible training data contains a plurality of data entries, each data entry containing the alimentary profile and nourishment information and a correlated nourishment score data; and
generating the nourishment score as a function of the score machine-learning process, wherein the score machine-learning process uses the alimentary profile and the nourishment information relating to the edible of interest as an input, and outputs the nourishment score.

11. A method of predicting alimentary element ordering based on biological extraction, the method comprising:
receiving, by a computing device, a plurality of biological extractions of a user;
identifying, by the computing device, a plurality of edibles, wherein identifying the plurality of edibles further comprises:
obtaining an alimentary element order chronicle of the user;
generating an alimentary profile as a function of a biological extraction of the plurality of biological extractions; and
identifying the plurality of edibles as a function of the alimentary profile;
generating, by the computing device and for the plurality of edibles, a plurality of nourishment scores, wherein generating the plurality of nourishment scores includes generating, for each edible of the plurality of edibles, a nourishment score as a function of the edible and the alimentary profile;
ordering, by the computing device, the plurality of edibles according to the plurality of nourishment scores;
displaying, by the computing device the ordered plurality of edibles;
receiving, by the computing device, a user input comprising a user-selected option regarding the plurality of edibles;
generating, by the computing device, a predicted biological extraction as a function of the user input, wherein generating the predicted biological extraction comprises:

training a machine-learning model on a training dataset comprising the alimentary element order chronicle and with the plurality of biological extractions; and determining the predicted biological extraction as a function of the user input and the trained machine-learning model;

displaying, by the computing device, using a graphical user interface, the predicted biological extraction;

determining, by the computing device, one or more alternative alimentary elements as a function of the predicted biological extraction; and determining, by the computing device, an alimentary element originator as a function of the one or more alternative alimentary elements using a radial search process, wherein the radial search process is based on rings, and wherein the radial search process iteratively modifies radii of the rings and generates new centers therefor to cover a search space.

12. The method of claim 11, wherein generating the alimentary profile further comprises:

receiving a biological extraction of the user; and generating the alimentary profile as a function of the biological extraction and the alimentary element order chronicle.

13. The method of claim 11, wherein generating the alimentary profile further comprises:

retrieving a performance profile; and generating the alimentary profile as a function of the performance profile and the alimentary element order chronicle.

14. The method of claim 11, wherein identifying the plurality of edibles further comprises:

receiving a datum as a function of an edible database; and identifying the plurality of edibles as a function of the alimentary profile and the datum.

15. The method of claim 11, wherein identifying the plurality of edibles further comprises:

receiving an element of user geolocation data; and identifying the plurality of edibles as a function of the alimentary profile and the element of user geolocation data.

16. The method of claim 11, wherein determining each nutrition score further comprises:

receiving nourishment information regarding an edible of the plurality of edibles; and determining the nutrition score as a function of the nourishment information.

17. The method of claim 16, wherein the nourishment information comprises a caloric input.

18. The method of claim 16, wherein the nourishment information comprises a nutrient input.

19. The method of claim 16, wherein the nourishment information comprises a nutritional impact.

20. The method of claim 11, wherein generating each nourishment score further comprises:

training a score machine-learning process using edible training data, wherein edible training data contains a plurality of data entries, each data entry containing the alimentary profile and nourishment information and a correlated nourishment score data; and generating the nourishment score as a function of the score machine-learning process, wherein the score machine-learning process uses the alimentary profile and the nourishment information relating to the edible of interest as an input, and outputs the nourishment score.

* * * * *